US 8,687,860 B2

(12) United States Patent
Gustafson

(10) Patent No.: US 8,687,860 B2
(45) Date of Patent: Apr. 1, 2014

(54) MAMMOGRAPHY STATISTICAL DIAGNOSTIC PROFILER AND PREDICTION SYSTEM

(75) Inventor: Greg Gustafson, Maple Plain, MN (US)

(73) Assignee: Penrad Technologies, Inc., Buffalo, MN (US)

( * ) Notice: Subject to any disclaimer, the term of this patent is extended or adjusted under 35 U.S.C. 154(b) by 1115 days.

(21) Appl. No.: 12/625,910

(22) Filed: Nov. 25, 2009

(65) Prior Publication Data

US 2011/0123073 A1    May 26, 2011

Related U.S. Application Data

(60) Provisional application No. 61/282,000, filed on Nov. 24, 2009.

(51) Int. Cl.
*G06K 9/00* (2006.01)
*G06K 9/46* (2006.01)

(52) U.S. Cl.
USPC ............................ 382/128; 600/300; 600/437

(58) Field of Classification Search
USPC ........................... 382/128, 190; 600/300, 437
See application file for complete search history.

(56) References Cited

U.S. PATENT DOCUMENTS

| | | | |
|---|---|---|---|
| 4,972,264 | A | 11/1990 | Bishop et al. |
| 5,021,770 | A | 6/1991 | Aisaka et al. |
| 5,212,637 | A | 5/1993 | Saxena |
| 5,229,585 | A | 7/1993 | Lemberger et al. |
| 5,241,659 | A | 8/1993 | Parulski et al. |
| 5,321,520 | A | 6/1994 | Inga et al. |
| 5,325,478 | A | 6/1994 | Shelton et al. |
| 5,343,390 | A * | 8/1994 | Doi et al. ............ 382/132 |
| 5,452,416 | A | 9/1995 | Hilton et al. |
| 5,565,678 | A | 10/1996 | Manian |
| 5,670,984 | A | 9/1997 | Robertson et al. |
| 5,708,810 | A | 1/1998 | Kern et al. |

(Continued)

FOREIGN PATENT DOCUMENTS

| | | |
|---|---|---|
| EP | 0487110 A2 | 5/1992 |
| WO | WO 03/046796 A2 | 6/2003 |

(Continued)

OTHER PUBLICATIONS

Definistion Syntehsize—the freedictionary.com as downloaded on Oct. 22, 2012.*

(Continued)

*Primary Examiner* — Luke Gilligan
(74) *Attorney, Agent, or Firm* — Patterson Thuente Pedersen, P.A.

(57) ABSTRACT

A method and system for analyzing and retrieving breast tissue abnormality tracking data, providing a tool for a radiologist that includes a report summarizing the statistical frequency of diagnosed patients, both locally and nationally, with mammogram region-of-interest classifications similar to the mammogram images taken of the anatomy of an individual patient. In one embodiment, a computer aided diagnostic program can be tested or verified against the mammography images and the region-of-interest classifications that have been validated by definitive patient diagnosis. Another embodiment allows the efficient collection of all of the mammogram abnormalities for a given medical facility in order to provide trending data or radiologist performance analysis. In yet another embodiment, the region-of-interest abnormalities in a single location in a patient's tissue are correlated across a variety of imaging modalities including X-rays, mammogram, CT, ultrasound, MRI, or other imaging technologies.

20 Claims, 16 Drawing Sheets

(56) References Cited

U.S. PATENT DOCUMENTS

| | | | |
|---|---|---|---|
| 5,719,567 A | 2/1998 | Norris | |
| 5,917,929 A | 6/1999 | Marshall et al. | |
| 5,940,188 A | 8/1999 | Kurozasa | |
| 6,006,191 A | 12/1999 | DiRienzo | |
| 6,047,257 A | 4/2000 | Dewaele | |
| 6,176,429 B1 | 1/2001 | Reddersen et al. | |
| 6,243,095 B1 | 6/2001 | Shile et al. | |
| 6,246,782 B1 | 6/2001 | Shapiro et al. | |
| 6,253,184 B1 | 6/2001 | Ruppert | |
| 6,260,021 B1 | 7/2001 | Wong et al. | |
| 6,311,419 B1 | 11/2001 | Inbar | |
| 6,317,617 B1 | 11/2001 | Gilhuijs et al. | |
| 6,347,241 B2 | 2/2002 | Burbank et al. | |
| 6,347,299 B1 | 2/2002 | Holzman et al. | |
| 6,349,143 B1 | 2/2002 | Hastings et al. | |
| 6,355,024 B1 | 3/2002 | Small et al. | |
| 6,434,262 B2 | 8/2002 | Wang | |
| 6,587,830 B2 | 7/2003 | Singer | |
| 6,614,921 B1 | 9/2003 | Chung et al. | |
| 6,629,378 B2 | 10/2003 | Gustafson | |
| 6,678,703 B2 | 1/2004 | Rothschild et al. | |
| 6,766,297 B1 | 7/2004 | Lamer et al. | |
| 6,785,358 B2 | 8/2004 | Johnson et al. | |
| 6,831,648 B2 | 12/2004 | Mukherjee et al. | |
| 6,901,156 B2 | 5/2005 | Giger et al. | |
| 6,909,795 B2 | 6/2005 | Tecotzky et al. | |
| 6,970,587 B1 | 11/2005 | Rogers | |
| 7,081,976 B2 | 7/2006 | Harrington | |
| 7,103,205 B2 | 9/2006 | Wang et al. | |
| 7,124,760 B2 | 10/2006 | Wong | |
| 7,146,031 B1 | 12/2006 | Hartman et al. | |
| 7,184,582 B2 | 2/2007 | Giger et al. | |
| 7,247,139 B2 | 7/2007 | Yudkovitch et al. | |
| 7,308,126 B2 | 12/2007 | Rogers et al. | |
| 7,321,668 B2 * | 1/2008 | Horie et al. | 382/103 |
| 7,418,119 B2 | 8/2008 | Leichter et al. | |
| 7,616,801 B2 | 11/2009 | Gkanatsios et al. | |
| 7,668,718 B2 | 2/2010 | Kahn et al. | |
| 7,783,094 B2 | 8/2010 | Collins et al. | |
| 2001/0041991 A1 | 11/2001 | Segal et al. | |
| 2001/0043742 A1 | 11/2001 | Melen | |
| 2002/0016718 A1 | 2/2002 | Rothschild et al. | |
| 2002/0070973 A1 | 6/2002 | Croley | |
| 2002/0107885 A1 | 8/2002 | Brooks et al. | |
| 2002/0139019 A1 | 10/2002 | Gustafson | |
| 2002/0161628 A1 | 10/2002 | Lane Poor, Jr. et al. | |
| 2003/0007598 A1 * | 1/2003 | Wang et al. | 378/37 |
| 2003/0013951 A1 | 1/2003 | Stefanescu et al. | |
| 2003/0026503 A1 | 2/2003 | Kallergi et al. | |
| 2003/0065705 A1 | 4/2003 | Santos-Gomez | |
| 2003/0103663 A1 * | 6/2003 | Li et al. | 382/131 |
| 2003/0110178 A1 * | 6/2003 | Woods et al. | 707/100 |
| 2003/0174873 A1 * | 9/2003 | Giger et al. | 382/128 |
| 2004/0034550 A1 | 2/2004 | Menschik et al. | |
| 2004/0085443 A1 * | 5/2004 | Kallioniemi et al. | 348/135 |
| 2004/0086158 A1 * | 5/2004 | Leichter et al. | 382/128 |
| 2004/0101206 A1 | 5/2004 | Morimoto et al. | |
| 2004/0111299 A1 | 6/2004 | Onishi | |
| 2004/0122702 A1 | 6/2004 | Sabol et al. | |
| 2004/0141661 A1 | 7/2004 | Hanna et al. | |
| 2004/0181412 A1 | 9/2004 | Menhardt | |
| 2004/0258287 A1 | 12/2004 | Gustafson | |
| 2004/0258291 A1 | 12/2004 | Gustafson | |
| 2005/0031177 A1 | 2/2005 | Langille et al. | |
| 2005/0049497 A1 * | 3/2005 | Krishnan et al. | 600/437 |
| 2005/0108060 A1 | 5/2005 | Sasano | |
| 2005/0123185 A1 | 6/2005 | Balasubramanian et al. | |
| 2005/0149360 A1 * | 7/2005 | Galperin | 705/2 |
| 2005/0171430 A1 | 8/2005 | Zhang et al. | |
| 2005/0177312 A1 | 8/2005 | Guerrant et al. | |
| 2005/0216314 A1 | 9/2005 | Secor | |
| 2005/0238216 A1 * | 10/2005 | Yoden | 382/128 |
| 2005/0244041 A1 | 11/2005 | Tecotzky et al. | |
| 2005/0244082 A1 | 11/2005 | Yamatake | |
| 2006/0058603 A1 | 3/2006 | Dave et al. | |
| 2006/0111937 A1 | 5/2006 | Yarger et al. | |
| 2006/0147099 A1 | 7/2006 | Marshall et al. | |
| 2006/0212317 A1 | 9/2006 | Hahn et al. | |
| 2006/0257009 A1 | 11/2006 | Wang et al. | |
| 2006/0274928 A1 | 12/2006 | Collins et al. | |
| 2007/0003119 A1 | 1/2007 | Roehrig et al. | |
| 2007/0038085 A1 | 2/2007 | Zhang et al. | |
| 2007/0041623 A1 | 2/2007 | Roehrig et al. | |
| 2007/0098243 A1 | 5/2007 | Gustafson | |
| 2007/0118384 A1 | 5/2007 | Gustafson | |
| 2007/0118399 A1 | 5/2007 | Avinash et al. | |
| 2007/0122021 A1 * | 5/2007 | Zingaretti et al. | 382/132 |
| 2007/0185732 A1 | 8/2007 | Hicks et al. | |
| 2007/0211930 A1 | 9/2007 | Dolwick et al. | |
| 2007/0274585 A1 * | 11/2007 | Zhang et al. | 382/132 |
| 2008/0019581 A1 | 1/2008 | Gkanatsios et al. | |
| 2008/0025592 A1 | 1/2008 | Jerebko et al. | |
| 2008/0130968 A1 | 6/2008 | Daw et al. | |
| 2008/0162352 A1 * | 7/2008 | Gizewski | 705/50 |
| 2008/0255849 A9 | 10/2008 | Gustafson | |
| 2008/0267470 A1 | 10/2008 | Zhang et al. | |
| 2008/0285825 A1 | 11/2008 | Zhang et al. | |
| 2009/0093711 A1 | 4/2009 | Hermosillo Valadez | |
| 2009/0129644 A1 | 5/2009 | Daw et al. | |
| 2009/0154782 A1 | 6/2009 | Zhang et al. | |
| 2009/0165009 A1 | 6/2009 | Heffernan et al. | |
| 2009/0171236 A1 | 7/2009 | Davies | |
| 2009/0171871 A1 | 7/2009 | Zhang et al. | |
| 2009/0185732 A1 | 7/2009 | Zhang et al. | |
| 2009/0192823 A1 | 7/2009 | Hawkins et al. | |
| 2009/0220138 A1 | 9/2009 | Zhang et al. | |
| 2009/0238421 A1 | 9/2009 | Zhang et al. | |
| 2009/0238422 A1 | 9/2009 | Zhang et al. | |
| 2009/0310843 A1 * | 12/2009 | Moriya | 382/131 |
| 2010/0086185 A1 * | 4/2010 | Weiss | 382/131 |
| 2010/0280375 A1 * | 11/2010 | Zhang et al. | 600/443 |
| 2011/0028825 A1 * | 2/2011 | Douglas et al. | 600/407 |
| 2011/0110576 A1 * | 5/2011 | Kreeger et al. | 382/132 |
| 2011/0123079 A1 | 5/2011 | Gustafson | |
| 2011/0137132 A1 | 6/2011 | Gustafson | |

FOREIGN PATENT DOCUMENTS

| | | |
|---|---|---|
| WO | WO 03/046796 A3 | 6/2003 |
| WO | WO 2005/003912 A2 | 1/2005 |
| WO | WO 2005/003912 A3 | 1/2005 |

OTHER PUBLICATIONS

Doi, "Current Status and future potential of computer-aided diagnosis in medical imaging" The British Journal of Radiology, 78 2005.*

Henry A. Swett, Pradeep G. Mutalik, Vladimir P. Neklesa, Laura Horvath, Carol Lee, Joan Richter, Irena Tocino, and Paul R. Fischer, Voice-Activated Retrieval of Mammography Reference Images, Journal of Digital Imaging, vol. 11, No. 2 May 1998: pp. 65-73.

GPCALMA: a Grid-based tool for Mammographic Screening. Authors: S. Bagnasco, U. Bottigli, P. Cerello, S.C. Cheran, P. Delogu, M.E. Fantacci, F. Fauci, G. Forni, A. Lauria, E. Lopez Tones, R. Magro, G.L. Masala, P. Oliva, R. Palmiero, L. Ramello, G. Raso, A. Retico, M. Sitta, S. Stumbo, S. Tangaro, E. Zanon. HealthGrid Workshop 2004. arXiv.org.

Application and File History of U.S. Appl. No. 12/625,926, filed Nov. 25, 2009, Inventor Gustafson.

Application and File History of U.S. Appl. No. 12/625,898, filed Nov. 25, 2009, Inventor Gustafson.

Application and File History of U.S. Appl. No. 10/418,191, filed Apr. 17, 2003, Inventors Schafer et al.

Selenia—User Guide / Administrator Guide, P/N 9-500-0293, Rev. 1, Copyright 2002-2003.

Application and File History of U.S. Appl. No. 11/443,742, filed May 31, 2006, Inventor Gustafson.

Application and File History of U.S. Appl. No. 11/603,554, filed Nov. 22, 2006, Inventor Gustafson.

Application and File History of U.S. Appl. No. 10/871,763, filed Jun. 17, 2004, Inventor Gustafson.

Application and File History of U.S. Appl. No. 10/871,740, Jun. 17, 2004, Inventor Gustafson.

(56) References Cited

OTHER PUBLICATIONS

Application and File History for U.S. Appl. No. 12/953,100 filed Nov. 23, 2010, inventor Gustafson.
PenRad, Mammography Information System awith R2 Checkmate Ultra CAD Connectivity Module. Copyright Sep. 18, 2002—REV. Jun. 16, 2004.
PenRad, "Technologist Mammography System Handbook", Copyright 1995-2003 rev. Jul. 7, 2003.
AuntMinnie, "Confirm, PenRad Steamline Breast MRI Reporting". Nov. 27, 2007.
PenRad, "PenRad CAD Connectivity Module" Copyright 1997-2003 rev. Jul. 2, 2003.
AuntMinnie, "A Guide to Digital and Soft-Copy Mammography" Jul. 21, 2005.
Altera, "Medical Imaging Implementation Using FPGAs" Apr. 2006.
AuntMinnie, "PenRad Highlights Mammography Management Tools" Nov. 7, 2005.
PenRad, "PenRad Mammography Information System". Copyright 1998-2003. Jul. 2, 2003.
Internet Archive-PenRad.pdf files, as downloaded on Apr. 24, 2012.
Hsu et al.,"SPIRS: A Web-based Image Retrieval System for Large Biomedical Databases", 21 pages. Sep. 26, 2009.

* cited by examiner

Right Breast Mammogram Abnormality Detailing | :Christine Jade Anderson, | 11/18/2009 20:28:38
Joanne W. Adamsick DOB: 09/01/1926 AGE: 83 F PID: 102828 SSN: 987654321

─ Ab Type ─
Seen/US only
Possible
Multiple
Cluster of
Various

┌─ ─ ─ ─ ─ ─┐
│ Mass      │
│ Mass solid│
│ Mass part solid│
│ Mass skin │
└ ─ ─ ─ ─ ─ ┘

─ Profile Ab ─
Shape
Irregular
Lobulated
Oval
Reniform
Round
Margin
Circumscribed
Indistinct
Microlobulated
Obscured
Spiculated
Density
High density
Low density
Equal density
Fat containing
Cent lucent ─ Changes ─
New
Not sig chg.
Stable
No long seen
Part removed
Incr in size
Decr in size
Less prom.
More prom.
Incr in number
Decr in number
Incr in calcs
Decr in calcs ─ Assoc Calc ─
Generic calcs
Amorphous
Branching
Coarse
Dystrophic
Eggshell
Fine
Heterogeneous
Indistinct
Large rodlike
Layering
Linear
Lucent centered
Milk of calcium
Pleomorphic
Punctate
Rim
Round
Skin
Spherical
Suture
Vascular
Calc Dist
Clustered
Diffuse
Grouped
Linear
Regional
Scattered
Segmental ─ Assoc Findings ─
Archit distortion  Post surgical so
Axillary adenop  Skin involvement
Brachy tube      Seroma
Bx clip          Skin lesion
Bx clips         Skin retraction
Chest wall inva  Skin thicken
Gold Seed        Surgical clip
Nipple retract   Surgical clips
Hematoma         Trab thicken ─ Corresponds with ─
US         sz <US     sz > US
MRI        sz <MRI    sz > MRI
Palpated   sz <palp   sz > palp
Pain       Tender     Incidental
Sc'tim     Ductog.    Pst-op chg
Redness    Concern    Skin marke ─ Not Prev Seen On ─
Clinical exam MRI
Mammogram Ductogram
Ultrasound ─ Special Circumstances ─
Addl Views     Dem By Prior
Confirm            Ultrasound
Do not Confirm     Aspiration
                   Biopsy
                   MRI Not sig If not palpable
Not on prev study
Visible ML only ─ Size/Dist/Axis ─
Ab dimensions>
Titles on report
Parallel/skin
Perpendic/skin
In skin
In mammary
Hide clock on rpt
Hide location
Use in/out/up/lo Add Text   OK   Cancel  Help   Set Def ─ Consistent with ─
Likely represents
Most likely
Resembles
w/ differential dia
Abscess
Carcinoma
Carcinoma know
Cluster of cysts
Cyst
Cyst Oil
DCIS
Fat necrosis
Fibroadenoma
Fibroad. degener.
Fibrocystic chang
Fibroglandular tis
Fibrosis
Hamartoma
Hematoma
Intramam node
Lipoma
Lymph node.
Mass Solid
Mastitis
Papillary lesion
Post surg scar
Post lumpec scar
Prev biopsy
Prev surgery
Prev trauma
Radical scar
Seroma
Skin lesion ─ Impression & Recs ─
2 Benign
3 Probably benign
4 Suspicious abnorm
4a Susp ab - low
4b Susp ab - interme
4c Susp ab - modera
5 Highly suggestive
0 Needs addl evaluat
6 Known BX / postiv
Post BX / marker
N/A m98:b44:t7062
m20K:b38K:t943K

Fig. 6b

Right Breast Mammogram Abnormality Detailing :Christine Jade Anderson, 11/18/2009 20:34:32
Joanne W. Adamsick DOB: 09/01/1926 AGE: 83 F PID: 102828 SSN: 987654321

— Ab Type —
Seen/US only
Possible
Multiple
Cluster of
Various

Mass
Mass solid
Mass part solid
Mass skin

— Size/Dist/Axis —
Ab dimensions>
Titles on report
Parallel/skin
Perpendic/skin
In skin
In mammary
Hide clock on rpt
Hide location
Use in/out/up/lo — Profile Ab —
Shape
Irregular
Lobulated
Oval
Reniform
Round
Margin
Circumscribed
Indistinct
Microlobulated
Obscured
Spiculated
Density
High density
Low density
Equal density
Fat containing
Cent lucent — Changes —
New
Not sig chg.
Stable
No long seen
Part removed
Incr in size
Decr in size
Less prom.
More prom.
Incr in number
Decr in number
Incr in calcs
Decr in calcs — Assoc Calc —
Generic calcs
Amorphous
Branching
Coarse
Dystrophic
Eggshell
Fine
Heterogeneous
Indistinct
Large rodlike
Layering
Linear
Lucent centered
Milk of calcium
Pleomorphic
Punctate
Rim
Round
Skin
Spherical
Suture
Vascular
Calc Dist
Clustered
Diffuse
Grouped
Linear
Regional
Scattered
Segmental — Assoc Findings —
Archit distortion Post surgical so
Axillary adenop Skin involvemen
Brachy tube   Seroma
Bx clip       Skin lesion
Bx clips      Skin retraction
Chest wall inva Skin thicken
Gold Seed     Surgical clip
Nipple retract Surgical clips
Hematoma      Trab thicken — Corresponds with —
US        sz <US     sz > US
MRI       sz <MRI    sz > MRI
Palpated  sz <palp   sz > palp
Pain      Tender     Incidental
Sc'tim    Ductog.    Pst-op chg
Redness   Concern    Skin marke — Not Prev Seen On —
Clinical exam MRI
Mammogram Ductogram
Ultrasound — Special Circumstances —
Add'l Views     Dem By Prior
Confirm            Ultrasound
Do not Confirm     Aspiration
                   Biopsy
                   MRI Not sig if not palpable
Not on prev study
Visible ML only — Consistent with —
Likely represents
Most likely
Resembles
w/ differential dia
Abscess
Carcinoma
Carcinoma know
Cluster of cysts
Cyst
Cyst Oil
DCIS
Fat necrosis
Fibroadenoma
Fibroad. degener
Fibrocystic chang
Fibroglandular tis
Fibrosis
Hamartoma
Hematoma
Intramam node
Lipoma
Lymph node.
Mass Solid
Mastitis
Papillary lesion
Post surg scar
Post lumpec scar
Prev biopsy
Prev surgery
Prev trauma
Radical scar
Seroma
Skin lesion — Impression & Recs —
<charge birads>
5 Highly suggestive
Unless previous sho
Ultrasound
Poss. Ultrasound
Biopsy
BX base on clinical
Clinical correlation
Diagnostic aspiration
FNA biopsy
MRI
MRI Biopsy
Needle loc. & surg b
US loc. & surg bx
Poss. core bx
Poss. stereo vac bx
Poss. US bx
Scintimammagraphy
Stereotactic core bx
Surgical Consult
Surgical consult & bx
Ultrasound guided bx
Vacuum Bx m2:b2:t121
m32:b8:t180

Add Text   OK   Cancel Help   Set Def

Right Breast MRI Abnormality Detailing  :Christine Jade Anderson, Penrad Main
Mrs. Patricia Leanne Meares  DOB: 09/01/1932  AGE: 76  F  PID: 4  SSN: 232323232323

| Ab Type | Profile Ab | Assoc Calc | Assoc Findings | Consistent with | Impression & Recs |
|---|---|---|---|---|---|
| Seen/US only | Shape | Generic calcs | Archit distortion | Post surgical so | Likely represents | <charge birads> |
| Possible | Irregular | Amorphous | Axillary adenop | Skin involvemen | Most likely | 5 Highly suggestive |
| Multiple | Lobulated | Branching | Brachy tube | Seroma | Resembles | Unless previous sho |
| Cluster of | Oval | Coarse | Bx clip | Skin lesion | w/ differential dia | Ultrasound |
| Various | Reniform | Dystrophic | Bx clips | Skin retraction | Abscess | Poss. Ultrasound |
|  | Round | Eggshell | Chest wall inva | Skin thicken | Carcinoma | Biopsy |
| Mass | Margin | Fine | Gold Seed | Surgical clip | Carcinoma know | BX base on clinical |
| Mass solid | Circumscribed | Heterogeneous | Nipple retract | Surgical clips | Cluster of cysts | Clinical correlation |
| Mass part solid | Indistinct | Indistinct | Hematoma | Trab thicken | Cyst | Diagnostic aspiration |
| Mass skin | Microlobulated | Large rodlike |  |  | Cyst Oil | FNA biopsy |
|  | Obscured | Layering | Corresponds with |  | DCIS | MRI |
|  | Spiculated | Linear | US | sz <US | sz > US | Fat necrosis | MRI Biopsy |
|  | Density | Lucent centered | MRI | sz <MRI | sz > MRI | Fibroadenoma | Needle loc. & surg b |
|  | High density | Milk of calcium | Palpated | sz <palp | sz > palp | Fibroad. degener | US loc. & surg bx |
|  | Low density | Pleomorphic | Pain | Tender | Incidental | Fibrocystic chang | Poss. core bx |
|  | Equal density | Punctate | Sc'tim | Ductog. | Pst-op chg | Fibroglandular tis | Poss. stereo vac bx |
|  | Fat containing | Rim | Redness | Concern | Skin marke | Fibrosis | Poss. US bx |
|  | Cent lucent | Round | Not Prev Seen On |  |  | Hamartoma | Scintimammography |

442

Abnormality Dimensions Selection  :Christine Jade Anderson, Penrad Main
Mrs. Patricia Leanne Meares  DOB: 09/01/1932  AGE: 76  F  PID: 4  SSN: 232323232323

| Size/Dist/Axis | Radial Size | Anti-rad Size | Trans Size | AP Size | Cranio Size | Nipple Size | Skin Size | Chest Size |
|---|---|---|---|---|---|---|---|---|
| Ab dimensions> | in cm | in cm | in cm | in cm | in cm | in cm | in cm | in cm |
| Titles on report | in mm | in mm | in mm | in mm | in mm | in mm | in mm | in mm |

[ OK ]  [ Cancel ]  [ Help ]

| | | Matching Statistical Information | :Christine Jade Anderson, Penrad Main Clinic | 11/18/2009 20:28:10 | |
|---|---|---|---|---|---|
| | | Joanne W. Adamsick DOB: 09/01/1926 AGE: 83 F PID: 102828 SSN: 987654321 | | | |
| | | Exams w/pathology: ID - Invasive ductal carcinoma | | | |
| | Sel | Date | Description | Patient Name | PID | Rad Name |
| 1 | ☐ | 09/12/1995 | Mammography Examination | Bruns, Joni J | 223241609 | Daskair, Tom, Md Re |
| 2 | ☐ | 12/14/1995 | Mammography Examination | Lee, Ann P | 73745 | Pobble, Robert, M.D |
| 3 | ☐ | 12/14/1995 | Mammography Examination | Lee, Julie P | 3755 | Anderson, Christine, |
| 4 | ☐ | 05/20/1996 | Mammography Examination | Dibernardo, Nancy O | 725717 | Carsen, Leo, MD |
| 5 | ☐ | 05/28/1996 | Mammography Examination | Nauve, Ella J | 9622857 | Anderson, Christine, |
| 6 | ☐ | 10/29/1996 | Mammography Examination | Mann, Ruthanne M | 56715 | Anderson, Christine, |
| 7 | ☐ | 03/09/2000 | Mammography Examination | Jensen, Anita W | 43460 | Anderson, Christine, |
| 8 | ☐ | 04/01/2000 | Mammography Examination | Kachel, Luella I | 223243960 | Anderson, Christine, |
| 9 | ☐ | 07/14/2000 | Mammography Examination | Cacy, Nila E | 0235 | Anderson, Christine, |
| 10 | ☐ | 07/23/2000 | Mammography Examination | Qq, Adele R | 323138 | Anderson, Christine, |
| 11 | ☐ | 07/06/2001 | Mammography Examination | Demcho, Andrene K | 743407 | Anderson, Christine, |
| 12 | ☐ | 12/09/2002 | Mammography Examination | Zamiska, Mary D | 54275 | Anderson, Christine, |
| 13 | ☐ | 08/18/2005 | Mammography Examination | Black, Nancy J | 223246201 | Anderson, Christine, |
| 14 | ☐ | 09/12/2005 | Mammogram | Landsberg, Deborah | 3483 | Anderson, Christine, |
| 15 | ☐ | 09/15/2005 | Mammogram | Soenpaa, Adeline K | 8823544 | Anderson, Christine, |
| 16 | ☐ | 10/17/2005 | Mammogram | Christian, Judy P | 223242014 | Anderson, Christine, |
| 17 | ☐ | 10/18/2005 | Mammogram | Kinbe, Ann T | 743584 | Anderson, Christine, |
| 18 | ☐ | 03/27/2006 | Mammography Examination | Bach, Gwendolyn V | 223239966 | Anderson, Christine, |
| 19 | ☐ | 03/27/2006 | Mammography Examination | Beal, Myra E | 223246122 | Anderson, Christine, |
| 20 | ☐ | 08/02/2006 | Mammogram | Adamski, Helen H | 223240137 | Zippy, Gregory, M.D. |

| View patient priors | Print List | Send Images to Viewstation | ☐ Show all exams with finding - unfiltered ☐ by procedure type or selections | Show Findings | Exit | Help |

Fig. 9

ComParisons and Prior Exams :Christine Jade Anderson, Penrad Main Clinic | 11/18/2009 20:30:50
Julie P. Lee DOB: 12/10/1930 AGE: 78 F PID: 3755

Select Exam Report for Review

| | Date | Description | Recall | Ris Proc# |
|---|---|---|---|---|
| 1 | 02/17/2004 | Bilateral Screening Mammography :birads 1 | 2 year screening | |
| 2 | 11/19/2002 | Bilateral Screening Mammography :birads 1 | 2 year screening | |
| 3 | 01/09/1996 | Bilateral Diagnostic Mammography :birads 1 | 1 year screening | |
| 4 | 12/14/1995 | Pathology | No Recall (discretio.. | |
| 5 | 12/14/1995 | Bilateral Screening Mammography :birads 1 | Immediate follow-up | |

View Full | Preview | Print | Send to Viewstation | Create CD | Notes-Yes | Exit | Help

Fig. 10

| Preview | :Christine Jade Anderson, Penrad Main Clinic | 11/18/2009 20:33:23 |
|---|---|---|
| Julie P. Lee  DOB: 12/10/1930  AGE: 78 F  PID: 3755 | | |

Golden Valley, Minnesota 55343

Fax: (763) 555-5555

BILATERAL SCREENING MAMMOGRAM: 12/14/1995
Comparison is made to exam dated: 4/24/1993 East Memorial Center.
The tissue of both breasts is predominantly fatty.
There is a 6 cm round high density mass with a spiculated margin in the right breast at 12 o'clock in the posterior depth as palpated. Compared to previous films, this mass is new.
No significant masses, calcifications, or other findings are seen in the left breast.
IMPRESSIONS: SUSPICIOUS OF MALIGNANCY
The mass in the right breast is suspicious of malignancy. A clinical correlation is recommended for the mass.

REPORT REFLECTS CURRENT DEMOGRAPHICS AND CODING OS OF 11/18/2009

The patient has been or will be contacted.

Dr. Christine Jade Anderson M.D.
cja/penrad:12/14/1995 13:17:57

Imaging Technologist: Rabbi Patty A. Ferdickson RT(R)(M), Penrad Main Clinic
letter sent: Biopsy Required
Mammo BI-RADS: 4 Suspicious abnormality

[Print Copy]  [◀] [▶]  [Close]

● Mammo - Mass ○ Mammo - Calc ○ MRI ○ US

CALC TYPE
☐ Generic calcs
☐ Amorphous
☐ Branching
☐ Coarse
☐ Dystrophic
☐ Eggshell
☐ Fine
☐ Heterogeneous
☐ Indistinct
☐ Large rodlike
☐ Layering
☐ Linear
☐ Lucent-centered
☐ Milk of calcium
☐ Pleomorphic
☐ Punctate
☐ Rim
☐ Round
☐ Skin
☐ Spherical
☐ Suture
☐ Vascular

CALC DIST
☐ Clustered
☐ Diffuse
☐ Grouped
☐ Linear
☐ Regional
☐ Scattered
☐ Segmental

ASSOC FINDING
☐ Archit distortion
☐ Axillary adenop
☐ Chest wall invas
☐ Nipple retract
☐ Hematoma
☐ Skin Involvement
☐ Seroma
☐ Skin lesion
☐ Skin retraction
☐ Skin thicken
☐ Trab thicken

Profile Matches
Total: 757
Malignant: 152
Benign: 264
No BX: 331
BX profile
% Malignant: 38
% Benign: 62

Matching Pathology from PenRad Statistical Database

| Result | National | Percent of | Code | Finding |
|---|---|---|---|---|
| malignant | 36 | 22.2% | CI | Comedocarcinoma (Intraductal) |
| malignant | 32 | 19.8% | ID | Invasive ductal carcinoma |
| malignant | 24 | 14.8% | * | Other malignant |
| malignant | 23 | 14.2% | DCIS | Ductal carcinoma in situ |
| malignant | 13 | 8.0% | II | Invasive and In-situ Cancer |
| malignant | 10 | 6.2% | DCH | Intraductal carcinoma, high grade |
| malignant | 7 | 4.3% | DCC | Intraductal comedocarcinoma with necrosis |
| malignant | 6 | 3.7% | DS | Noninvasive, Intraductal carcinoma |
| malignant | 6 | 3.7% | PC | Papillary Carcinoma in-Situ |
| malignant | 5 | 3.1% | DCL | Intraductal carcinoma, low grade |
| benign | 37 | 14.0% | FA | Fibroadenoma |
| benign | 37 | 14.0% | DHU | Ductal Hyperplasia, Usual |
| benign | 36 | 13.6% | AD | Adenosis |
| benign | 35 | 13.3% | * | Other benign |
| benign | 27 | 10.2% | FC | Fibrocystic changes |
| benign | 19 | 7.2% | ADH | Hyperplasia, Atypical ductal |
| benign | 16 | 6.1% | AM | Apoctrine Metaplasia |
| benign | 10 | 3.8% | SA | Adenosis, Sclerosing tumor |
| benign | 10 | 3.8% | * | Fibrosis |
| benign | 9 | 3.4% | BCL | Benign calcifications |
| benign | 9 | 3.4% | BC | Cysts |
| benign | 4 | 1.5% | FNS | Fibroadenoma, NOS (not otherwise specified) |
| benign | 3 | 1.1% | NOS | - high risk |
| benign | 3 | 1.1% | FAL | Fibroadenolipoma |
| benign | 3 | 1.1% | IF | Inflammatory pseudotumors, Inflammation |
| benign | 3 | 1.1% | IP | Intraductal Papilloma |
| benign | 3 | 1.1% | FN | Inflammatory pseudotumors, Fat necrosis |

MAMMOGRAPHY STATISTICAL DIAGNOSTIC PROFILER AND PREDICTION SYSTEM

RELATED APPLICATIONS

This application claims the benefit of U.S. Provisional Application No. 61/282,000, entitled "MAMMOGRAPHY INFORMATION SYSTEM" and filed Nov. 24, 2009, which is incorporated herein by reference in its entirety.

The following co-pending patent applications of common assignee contain some common disclosure: "Multiple Modality Mammography Image Gallery and Clipping System," and "Mammography Information System," each filed on Nov. 25, 2009, and having Ser. Nos. 12/625,926 and 12/625,898, respectively, which are incorporated herein by reference in their entireties. A copy of each of the above-identified related applications is attached hereto as Appendix A and Appendix B.

TECHNICAL FIELD

The invention relates to the management and analysis of medical data and more specifically to the use of such data acquired from computer aided detection and clinician analysis of multiple imaging modalities in a clinician support tool.

BACKGROUND OF THE INVENTION

Historically, interpretation and diagnosis of mammograms and other medical image analysis has been performed using hardcopy x-ray films viewed on an alternator that typically allows x-ray films to be illuminated and masked for diagnostic viewing. Newer technology allows a radiologist or other medical professional to view mammograms and other diagnostic images electronically on high-resolution monitors. These images can also be digitally stored and transmitted across secure networks for archiving or review by other professionals.

A radiologist generally begins his or her review process by reviewing a patient's background information relevant to a radiology study, such as a patient's name, age, and any applicable medical conditions or risk factors. After reviewing the background information, the radiologist views multiple images created by radiological, X-ray, computed tomography (CT), ultrasound, magnetic resonance imaging (MRI), tomosynthesis, or other imaging technique of the patient's breast, or other organ, and dictates or uses a computerized information system to track findings, create reports, and make recommendations for future examinations. Such findings can include information pertaining to tissue density, the presence of masses, cysts, calcifications and other abnormalities, or any other breast tissue characteristics.

While there has been recent debate regarding the frequency at which women should undergo regular mammogram screenings, and at what age such screenings should begin, it is unlikely that the relatively quick and typically effective practice of mammography screening for breast cancer will disappear completely. Accordingly, there will continue to be a need for radiologists to view and interpret the images generated from patient examinations and screenings. Because the risk of breast cancer threatens the lives of many women, especially those over age 40, radiologists are often inundated with large numbers of mammogram images that must be viewed and, if abnormalities are present, categorized in order to determine if further examination is required. The developments in advanced patient imaging techniques, such as MRI, are also increasing the raw number of images that a radiologist can review. Therefore, there is an ongoing need to improve the speed and efficiency of the radiologist's review of the mammogram images, without sacrificing accuracy, and preferably with the smallest number of false-positive diagnoses. Additionally, given that mammograms are taken periodically, such as annually or biannually, once screening begins for a particular woman, there is also a need to manage, track and analyze data taken over a period of years or decades for a woman.

One commercially available computerized mammography information system (MIS) is the PenRad Mammography Information System, which is able to electronically track abnormalities, generate statistics, and provide patient correspondence. The PenRad™ system is described in copending U.S. patent application Nos. 12/625926 and 12/625898, filed on Nov. 25, 2009, which are incorporated herein by reference, and is available from PenRad. This system provides for the digital correlation of patient data related to a mammography or other diagnostic imaging procedure.

Legislation has mandated that mammography facilities track positive mammography findings and correlate such findings with biopsy results, maintain statistics for mammography medical outcome and analysis audits on each physician, and provide direct written notification to all patients of their exam results. The generation and correlation of this data is maintained locally by each medical center for each patient.

One system for categorizing this information is the Breast Imaging-Reporting and Data System (BI-RADS) published by the American College of Radiology (ACR). BI-RADS provides a system of mammography assessment categories in the form of standardized codes assigned by a radiologist during or after the viewing and interpretation of a medical image. BI-RADS allows for concise and unambiguous understanding of patient records between multiple radiologists and medical facilities. Consequently, a large number of mammogram images, biopsy results, and diagnosis statistics are potentially available in a patient-anonymous format, if necessary, in compliance with the Health Insurance Portability and Accountability Act of 1996 (HIPAA).

Recently, Digital Imaging and Communications in Medicine (DICOM) systems have become the accepted format for medical imaging systems. This format provides for the distribution and viewing of medical studies and images across a variety of platforms. The use of DICOM has, among other things, enabled industry compatibility and improved workflow efficiency between imaging and other information systems located in various healthcare environments. Currently, the DICOM standard is an 18-part publication, PS 3.1-2008 through PS 3.18-2008 describing a standard for digital imaging and communications in medicine developed by the American College of Radiology (ACR) and the National Electrical Manufacturers Association (NEMA) which is hereby incorporated by reference in its entirety. Among other elements, the DICOM standard provides a method of uniquely numbering any image or other information object to facilitate the unambiguous identification of images or information objects as they are viewed or manipulated in a system or transported across a network.

Conventional imaging systems enable a DICOM server to provide medical images across a network to various DICOM compatible clients on the network. Some examples of DICOM clients include picture archiving and communications systems, softcopy workstations, computer-aided diagnosis (CAD) systems, DICOM compatible CD or DVD burners, and other network system devices known to those skilled in the art. One example of a standards-based medical imaging environment is disclosed in U.S. Pat. No. 6,909,795, to Tecotzky et al., incorporated herein by reference.

SUMMARY OF THE INVENTION

Embodiments of the invention relate to systems and methods for analyzing and retrieving patient abnormality data for use with a CAD or mammography information system as part of or in conjunction with the diagnosis and interpretation of patient images such as x-ray mammograms, CT scans, MRI, and ultrasound images constructed from echoes, as well as pathologic images, that substantially meets the aforementioned needs of the industry.

In an embodiment, a method comprises obtaining a categorization of a region of interest in an image of a breast, comparing the categorization with a digitally stored database of existing categorizations of regions of interest, and determining a statistical likelihood of a diagnosis of the categorization based on the comparing.

In an embodiment, a mammographic image profiler comprises a database of existing categorizations of regions of interest in mammographic images, a graphical user interface configured to present a plurality of possible characteristics according to which a current categorization of a region of interest in a mammographic image can be defined, and a processor configured to identify existing categorizations in the database that match the current categorization and to present information related to the identification in the graphical user interface.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The embodiments of the present invention may be more completely understood in consideration of the following detailed description of various embodiments in connection with the accompanying drawings, in which:

FIG. 2 is an example of a mammography exam data-form suitable for use with embodiments of the invention.

FIG. 6*a* is another example embodiment of a ROI data entry form for use with embodiments of the invention.

FIG. 6*b* is the ROI data entry form of FIG. 6*a* with additional ROI categorizations entered.

FIG. 6*c* depicts two additional exemplary embodiments of ROI data entry forms for use with embodiments of the invention.

FIG. 7 is an example of a form showing the statistical analysis of a ROI.

FIG. 8 is an example of a form showing available images that match statistical analysis of the ROI of FIG. 7.

FIG. 9 is an example of a form showing a patient's exam history.

FIG. 10 is an example embodiment of a report generated according an embodiment of the invention.

FIG. 12 is an example embodiment of a web-based form for use with an embodiment of the invention.

Figure 1:
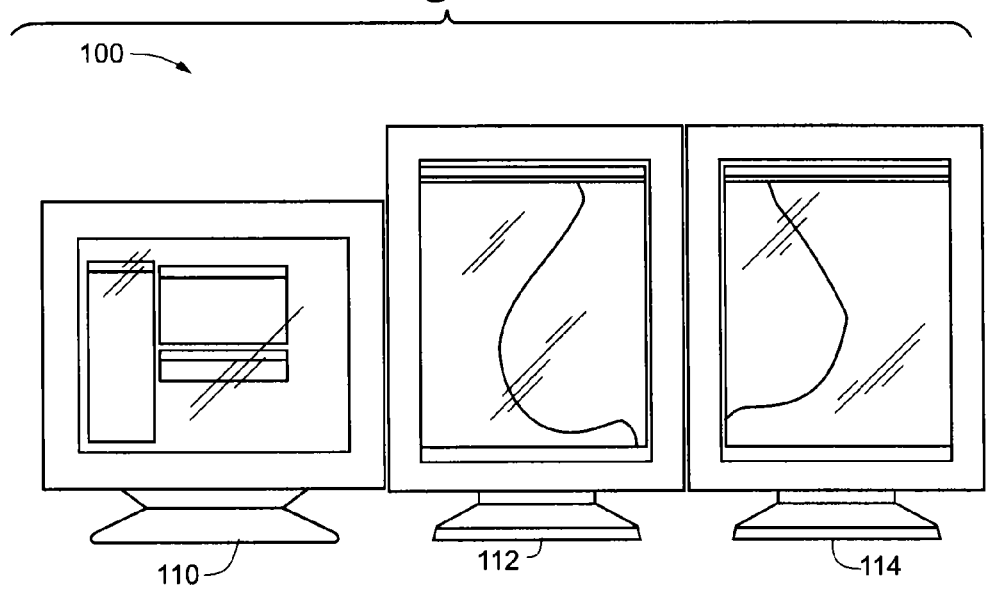
FIG. 1 is an example mammogram information system (MIS) display workstation according an embodiment of the invention.

While the present invention is amenable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention as defined by the appended claims.

DETAILED DESCRIPTION OF THE DRAWINGS

The increasing availability and quantity of digital information representing patient medical data and diagnostic images has created a need for a system that allows a doctor or radiologist to quickly access multiple diagnostic images that may be similar to an individual patient's condition. Access to images where the pictured abnormality has been definitively diagnosed can assist with the doctor or radiologist's diagnosis of the new patient's individual condition. Prior to the electronic production, archival, and detailed categorization of patient images, such comparisons were limited to a handful of common abnormalities described in the various medical texts or required laborious manual review of individual patient files.

Additionally, the availability of this collection of mammography images and their associated biopsy results presents an opportunity for statistical analysis of the likelihood that a matching region of interest (ROI) in an individual patient's mammography images is malignant or benign and whether or not a biopsy or further imaging should be ordered. Therefore, there is a need for a system that will quickly allow a radiologist to classify a ROI in a mammogram or other image and correlate the ROI to a large pool of existing data samples that have been definitively diagnosed in order to improve the accuracy and efficiency of patient diagnosis. The radiologist can be assisted in the classification of the ROI by a CAD module by automatically detecting potential ROI abnormalities or simply reducing the number of physical or verbal actions needed by the radiologist to enter the ROI classifying data.

In an example embodiment, a MIS is provided for use by a radiologist or other medical professional that preloads all of an individual patient's medical images for a specific portion of the patient's anatomy, regardless of the modality used to create the images. For example, in a breast cancer screening, any available x-ray, ultrasound, MRI, biopsy, or other images for the patient are retrieved and preprocessed by an appropriate CAD algorithm. A CAD module for the appropriate image type can isolate one or more ROI for review in an individual image. The disclosed invention takes these individual CAD results and correlates any common ROI findings between images of the same or different modalities. A summary "map" or outline of the examined patient's anatomy is then generated and displayed for the medical professional along with any other details about the potential ROI(s) that were generated by the CAD module(s).

In an example embodiment, the method of analyzing and retrieving abnormality tracking data provides a report of the statistical frequency of diagnosed patients both locally and nationally with mammogram ROI classifications similar to an individual patient. The abnormality data can include information disclosing the frequency of similar ROI classifications have been biopsied and the number of biopsies that were malignant or benign. The disclosed method of capturing and reporting abnormality tracking data provides a radiologist or other medical professional a tool to assess the likelihood of a ROI being malignant or benign, and whether or not the patient should undergo additional testing. The system then presents these statistics to the radiologist who can then choose to look further into the underlying related data if he or she desires.

The statistical mammography predictive system according to the present invention provides instantly and continually updated outcome statistics to a medical professional. The system utilizes the information and data points for each and every abnormality found by radiologists at a facility that have been entered into a mammography information system. As more patients are definitively diagnosed and their pathology records updated in the system, the greater the chances that an individual patient will have a condition similar to a previously diagnosed and imaged condition. This system can be integrated into an existing MIS or utilized as a standalone interface providing access to a large sample of mammogram abnormality data.

The system also provides an efficient mechanism for creating a comprehensive collection of abnormality data for a variety of pathology types. The collection comprising a uniform lexicon of classifications that allows for further analysis and study of the data while still maintaining patient privacy as required by the applicable law. Only unique copies of each combination of tracing data points must be kept in the system. As duplicate data is accumulated the counters of the abnormality and its diagnosis as benign or malignant are incremented. This aggregation of data creates a compact and anonymous abnormality database for the medical location. If desired, a complete reference of all abnormality data can be maintained. Those skilled in the art of developing and maintaining electronic databases will appreciate and understand the tradeoffs associated with the storage requirements necessary for the implementation of the contemplated system.

As numerous patient imaging facilities implement this non-patient identifying (and HIPAA compliant) data can be transferred to a central location accumulating an more complete database of abnormalities and the corresponding benign or malignant counters for each combination of tracking points and pathology type. Therefore, the large number of recorded abnormalities can be culled down to a manageable set of unique combinations specified by radiologists around the country. This culling, or grouping of duplicate abnormalities, allows for a medical professional to access a comprehensive database of the known set of abnormalities nearly instantaneously.

In a further embodiment, the system disclosed provides a mechanism to evaluate, validate, and improve any of a variety of existing CAD modules and techniques by providing an efficient platform for testing the cad module or technique against a wide variety of known, physician evaluated, and definitively diagnosed, patient abnormalities or ROI.

The invention can be better understood by reference to FIGS. 1-14. FIG. 1 illustrates an example embodiment of a mammogram display workstation 100. A typical mammogram display workstation 100 includes a controller display system 110 and at least one high-resolution image monitor 112. One or more additional high-resolution image monitor units 114 can also be used to provide additional viewing area to provide for the comparison of two or more images at full resolution. The controller display system 110 is any of a variety of commonly available video display monitors coupled to a personal computer such as an IBM-PC or compatible system running a version of the Microsoft WINDOWS operating system, or the equivalent thereof. In an embodiment, the image monitors 112 and 114 are liquid crystal displays (LCDs) that provide high-resolution and enhanced contrast for ease of viewing images, but may also be a cathode ray tube or other appropriate display in other embodiments. An exemplary image monitor can display approximately 2500×2000 pixels, although a variety of image monitor sizes are contemplated. In one embodiment, the mammogram display workstation 100 includes a server computer (not shown) that runs DICOM communications components of the mammogram display workstation 100; alternatively, this DICOM software may run on the controller display system 110. In yet another embodiment, a server computer is included that runs an Archived Image Retrieval service; alternatively, this software may also run on the controller display system 110 or on the DICOM compliant server.

Figure 2:
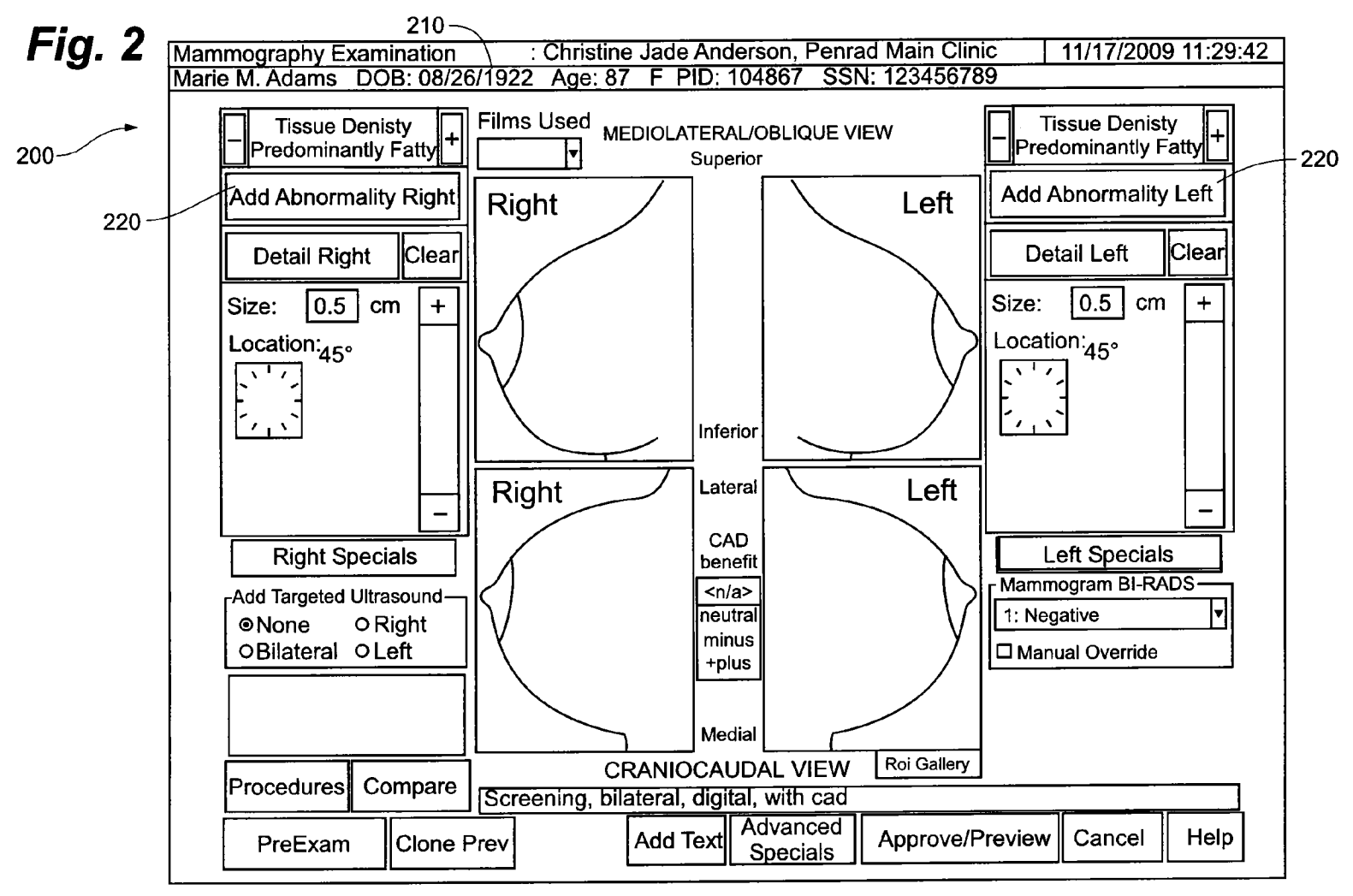

FIG. 2 illustrates an example embodiment of a medical diagnostic system that includes an abnormality-summary window 200. Abnormality-summary window 200 provides a convenient patient information summary 210 and an interface to import or enter additional data. In window 200 the radiologist can enter abnormality data for either the left or right breast by clicking on an "Add Abnormality" button 220. Additionally, a user can import a CAD report detailing any abnormalities that have been detected by existing CAD software. Examples of suitable CAD software include the CadStream product by Confirma or the B-CAD product by Medipattern.

Figure 3:
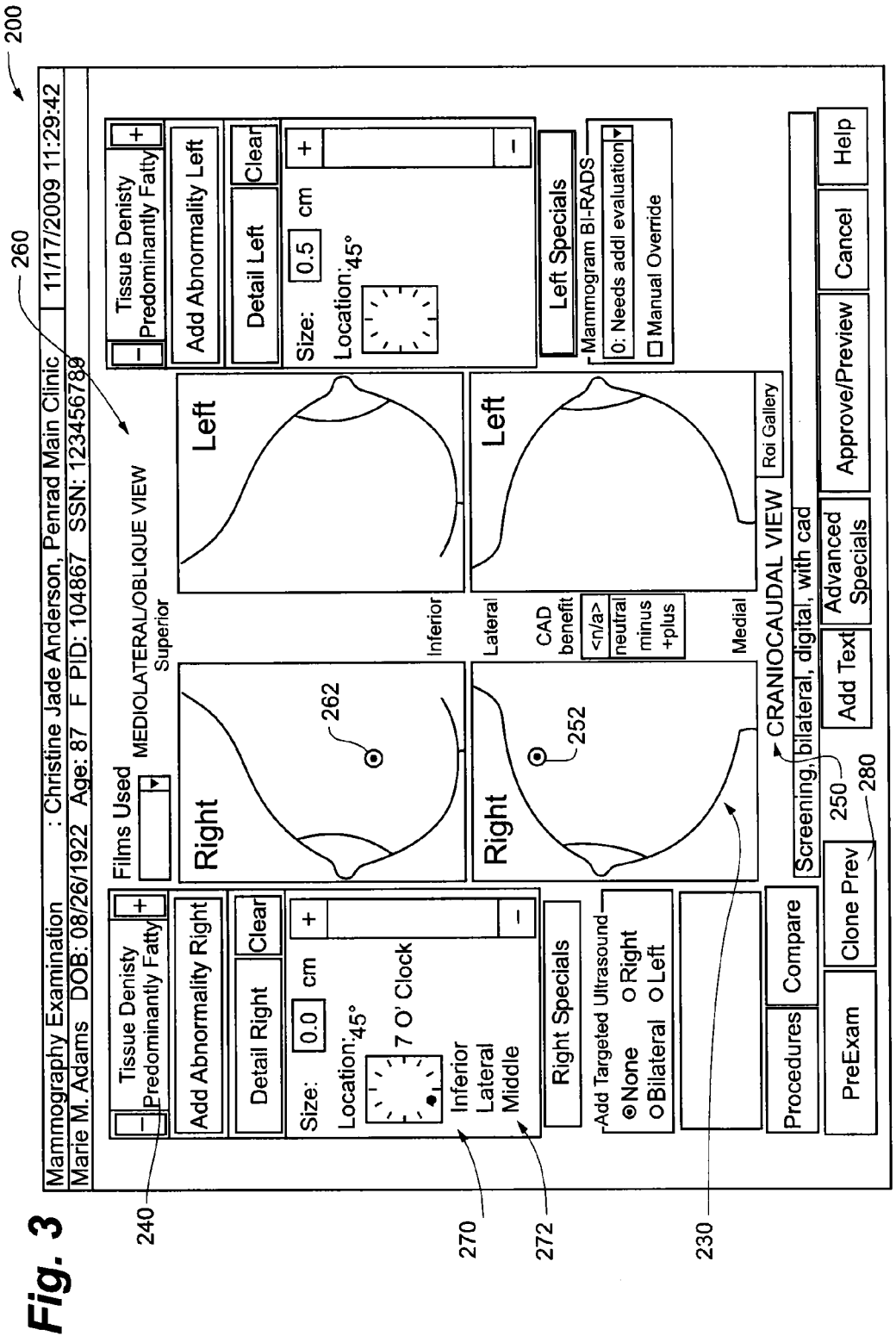
FIG. 3 is an example of the mammography exam data-form of FIG. 2 indicating a region of interest (ROI).

As shown in FIG. 3, imported CAD information stored in compliance with a pre-determined system such as BI-RADS is used to generate a wire-frame map or guide 230 depicting the location and depth of a ROI in or on a patient's anatomy that was detected by the CAD software or entered manually by a radiologist. The density of the patient's tissue is also presented in selector 240. The guide 230 includes both a craniocaudal (CC) view 250 and a mediolateral/oblique (ML) view 260 of both the left and right breasts of a patient. The ROI is depicted by the craniocaudal mark 252 and the mediolateral mark 262. In other situations, an abnormality may only be visible in one or the other of the ML or the CC view and, accordingly, only a single mark would be displayed in either the craniocaudal (CC) view 250 or the mediolateral/oblique (ML) view 260.

In an embodiment, the ROI data underlying either craniocaudal mark 252 or mediolateral mark 262 can be represented as the number of pixel spaces from at least two edges of the original image represented by the ROI. The retention of the number of pixels from at least two edges provides for the derivation of the location of the ROI on the original image. This allows the storage of multiple ROI for a single high-resolution image without the need to store multiple copies of the high-resolution image or even high-resolution clippings. It also permits derivation or mapping of an ROI in one image to other images based on known pixel sizes and edge distances.

In another alternative embodiment, the data underlying these two marks are used to then calculate an approximate location of the abnormality as viewed by a physician when facing the patient. This calculation also compensates for the fact that during the creation of a mammography image, the patient's breast is compressed to increase the amount of viewable tissue in the two-dimensional x-ray image. Additionally, compensation must be made for the angle at which the mediolateral/oblique view 260 is taken relative to the craniocaudal view 250 during mammogram imaging. Those skilled in the art will appreciate that the two views are not necessarily created at angles exactly perpendicular to each other due to the wide variety of patient anatomy and the need to capture as much tissue as possible in each image. The resulting combination of the craniocaudal data and the mediolateral data produce the clock-position 270 as shown for the exemplary ROI. This calculation is not possible if the ROI is only visible on a single image, as both a craniocaudal and mediolateral position are required, along with a distance either from the patient's nipple or chest wall to calculate the location of the ROI in three-dimensional space.

An abnormality does not need to be located or seen in both views to be characterized. Often in mammography an abnormality is only seen in one view and additional imaging is conducted to confirm its location in another view. The additional imaging can also reveal superimposed tissue, a situation in which the breast tissue of several layers was compressed together causing a potential mass seen in a single image with the appearance of an actual abnormality. A radiologist viewing multiple images of the same tissue area can appropriately categorize these situations.

Also shown in FIG. 3 is a three-word indication 272 of the location of the ROI in the patient's breast. In this example the ROI is located in the inferior (lower), lateral (outside), middle (distance between the chest and nipple) portion of the patient's right breast. Similar terms for the remaining quadrants and depth are provided by the ACR guidelines and will be understood by those skilled in the art.

An additional feature of the system is the capability of importing any ROI from a patient's previous examination that are already present in the system's database. A radiologist or technician can select the "Clone Prey" button 280 to review and import data from a previous examination. This feature further eliminates the need for duplicated effort on the part of the medical professional conducting the review of the patient's exam images.

Figure 4:
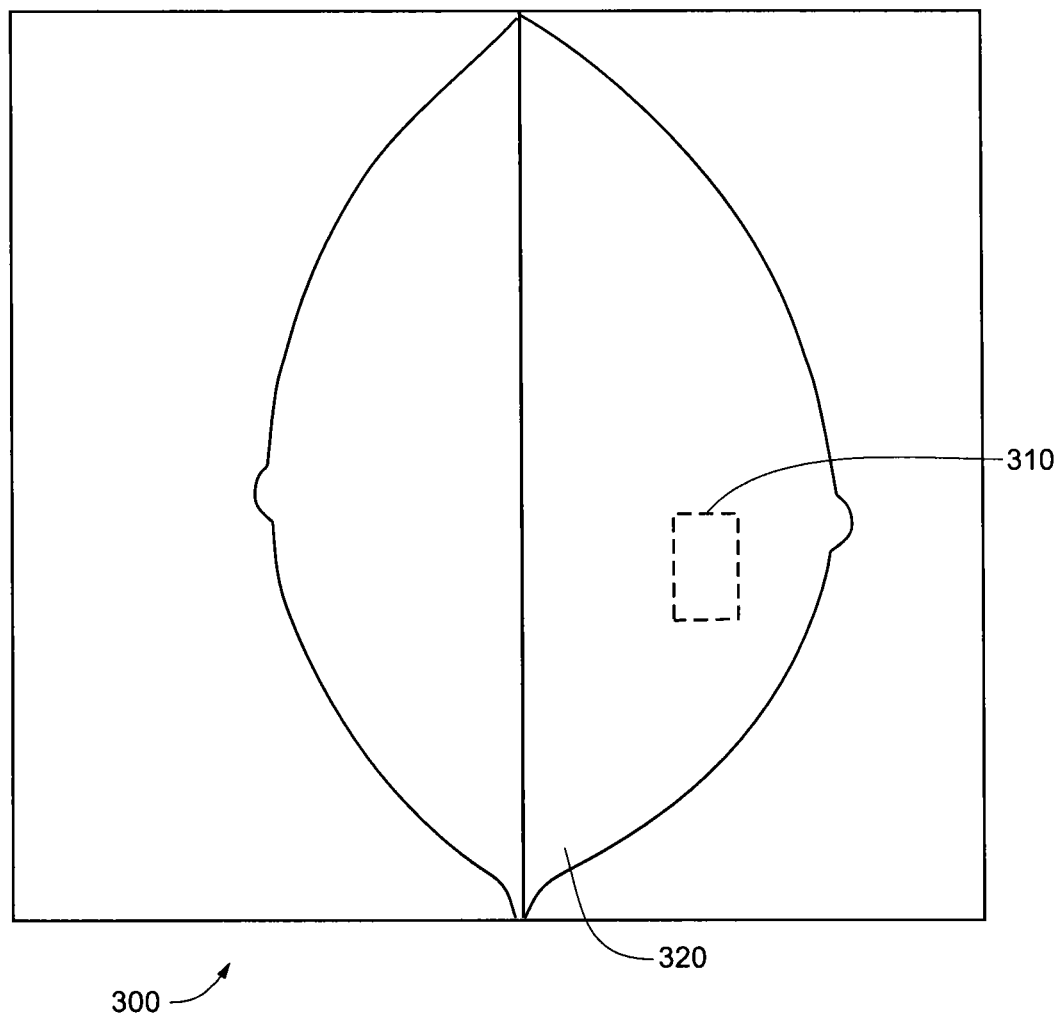
FIG. 4 is an example of a mammogram image with an ROI indicated.
Figure 5:
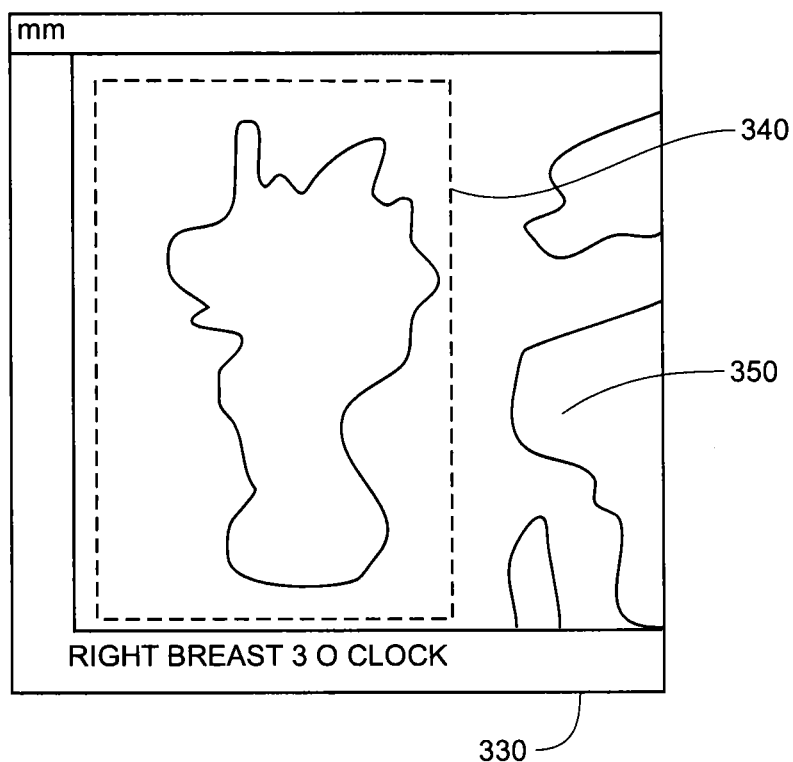
FIG. 5 is an example of an ultrasound image with an ROI indicated.

The system is capable of handling a variety of imaging technologies. FIG. 4 depicts an exemplary x-ray generated mammogram image 300 with an ROI indicated by a dashed outline 310 on the image 300 of the patient's breast tissue 320. FIG. 5 depicts an exemplary ultrasound image 330 with an ROI indicated by a dashed outline 340 on the image 330 of the patient's breast tissue 350. While the type of information depicted in a mammogram image 300 is clearly different from the ultrasound image 330, the system maintains the ROI indicated on each respective image by storing the coordinates of each ROI as an offset, in one embodiment utilizing the number of pixels, from at least two edges of the original digital image, regardless of the technique employed to generate the image. These coordinates are then used to calculate the distance from the patient's chest wall, nipple, or other appropriate reference point, to determine the measurements defining the location of the ROI. Similar techniques can be applied to other imaging technologies such as MRI or CT images that are capable of being stored in a standardized digital format where the correlation of the number of pixels in the image to the real-world distance depicted in the image is known.

FIG. 6a depicts an embodiment of an abnormality-detailing window 400. The detailing window 400 provides an interface for a radiologist to enter or view the detailed attributes that describe an abnormality in a selected ROI. FIG. 6a depicts the single attribute 402 of a "Mass" as being selected to describe the ROI depicted in FIG. 3. As indicated by the system, the presence of a mass alone is generally not enough to indicate the presence of a malignancy. The radiologist can then select an impression 404 and an appropriate recommendation 404 in the "Impression & Recs" area 406. In one embodiment, the system suggests an impression or recommendation in area 406 based on other selected attributes in window 400, which can then be reviewed by the radiologist and altered, if desired. The system can also dynamically and automatically adjust the selection in area 406 if other attributes in window 400 are changed during review. In other embodiments, area 406 is selectable by a radiologist or doctor.

The abnormality-detailing window 400 can include a profiler button 410 that provides a count of matching abnormalities and their pathological outcome. The profiler button 410, or another appropriate window, displays the number of biopsies performed that were diagnosed as malignancies 412, the number of biopsies performed that were diagnosed as benign 414, and the total number of matching abnormalities 416 in the database. The sum of the number of malignancies 412 and the number of benign 414 is the total number of biopsies performed on abnormalities possessing the same attributes selected in detailing window 400 at that location. The second line 418 of profiler window 410 displays these same quantities found in a national database. As discussed above, the single attribute of a Mass 402 in FIG. 6a yields a relatively low number of malignancies 412 (roughly 1.4%) of similar abnormalities in the local database. The combination of the number of malignancies 412 and the number of benign 414 is also a low percentage of the total number of similar abnormalities, indicating a low frequency of requests by the patient's physician for a biopsy. The profiler button 410 is depicted in the lower corner of the screen to provide a convenient, yet out of the way area to present statistical information. Other locations or embodiments, such as a floating window that can be repositioned by the radiologist are contemplated.

Two database versions are typically present in every system—one is the "local" version containing the data specific to the medical facility where the system is installed. This local data can be subsequently uploaded to a centralized server to be integrated with into a "regional," "national," or "global" version of the database. This allows individual users to compare their own facility's results with a larger sample of results. Additionally, the "local" version can be linked to the on-site examination image data, allowing the radiologist to see other examinations related to a specific pathology finding or set of characteristics. The radiologist can then nearly instantly view selected examinations, images, or specified regions of interest retrieved from the local database. The system can also be configured to link to information and retrieve images from the larger databases, although in one embodiment this can be done without any patient identifying information.

FIG. 6b depicts the abnormality-detailing window 400 of FIG. 6a, with three additional characteristics that describe the ROI. The Mass 402 is characterized as "Irregular" 420, "Microlobulated" 422, and having a "High density" 424. In the "Impression & Recs" area 406 the addition of the "5 Highly suggestive" 426 attribute indicates that a follow-up examination of the patient is necessary. In this case, the radiologist has selected the "Ultrasound guided bx" option 428, indicating that the recommended next step for the patient is an ultrasound-guided biopsy of the abnormality.

The addition of the three ROI characteristics in FIG. 6b significantly narrowed the number of matching abnormalities in the MIS database as shown in the profiler button 410. While only half of the biopsied abnormalities resulted in a result of malignancy 412 for the local database, as seen in the national database line 418, the vast majority of biopsied abnormalities of this type were malignant. While the relatively low number of data points presented for this abnormality type may not be sufficient to draw any definitive conclusions, this example shows the utility of being able to compare a local sample with a larger multi-site database of abnormalities providing an indication to the local medical personnel that further review of this abnormality scenario may be required. Those skilled in the medical and radiology arts will appreciate these and other advantages that this collection of data and the ease of access provided by the system yield.

FIG. 6c depicts another example of a right breast MRI abnormality-detailing window 440 and an example of an MRI abnormality-dimensioning window 442. These two windows display the BI-RADS compatible data points, optionally generated by a CAD software package used to pre-evaluate and generate the ROI in the MIS. In one embodiment, the CAD software package can populate the various fields presented by an abnormality window, such as exemplary MRI abnormality-dimensioning window 442. These widows also provide a radiologist with an interface to adjust, re-characterize, correct, add, or remove the ROI data based on their professional assessment of the ROI depicted in the patient's images. As depicted, in abnormality-dimensions window 442 a radiologist can quickly select or change the radial size, anti-radial size, transverse size, AP size, cranio size, distance from the nipple, distance from the skin, and distance from the chest, of the abnormality. Other appropriate measurements or mechanisms for entering these values are also contemplated.

The system contemplated in the example embodiment dynamically updates the values shown in the profiler button 410, of FIG. 6b, every time a new attribute is selected in abnormality-detailing window 400. One embodiment can achieve this high access speed by assigning an enhanced version of ACR lexicon descriptors to individual bits in a group of integers. This approach also yields a relatively compact database size, further minimizing search time. The tables below provide an exemplary sampling of potential abnormality lexicons. Each item in a lexicon is assigned a value. In Table 1, the STATS_VALUES field first provides a specified index into a list of database field values. These database fields are assigned indexes numbered 0 to n−1. The second hexadecimal value is the actual value assigned to the individual lexicon item. When this item is selected during an examination, the specified bit value is set in the assigned integer field using a bitwise OR operation. The LISTBOX_NAME column provides the general description of where on the abnormality-detailing window 440 the attribute would be grouped. The ITEM_NAME column provides the detailed characteristic that a radiologist can select when characterizing a patent image.

TABLE 1

Mammogram Lexicon Item Detailing

| LISTBOX_NAME | ITEM_NAME | STATS_VALUES |
| --- | --- | --- |
| Specify Abnormality | Fibrocystic tissue | 0,0x00000001 |
| Specify Abnormality | Cyst simple | 0,0x00000002 |
| Specify Abnormality | Mastitis area | 0,0x00000004 |
| Specify Abnormality | Mass solid | 0,0x00000008 |
| Specify Abnormality | Lesion | 0,0x00000010 |
| Specify Abnormality | Cyst | 0,0x00000020 |
| Specify Abnormality | Abscess | 0,0x00000040 |
| Specify Abnormality | Mass | 0,0x00000080 |
| Specify Abnormality | Papillary lesion | 0,x000000100 |
| Profile Abnormality | Irregular | 1,0x00000001 |
| Profile Abnormality | Lobulated | 1,0x00000002 |

TABLE 1-continued

Mammogram Lexicon Item Detailing

| LISTBOX_NAME | ITEM_NAME | STATS_VALUES |
| --- | --- | --- |
| Profile Abnormality | Oval | 1,0x00000004 |
| Profile Abnormality | Reniform | 1,0x00000008 |
| Profile Abnormality | Round | 1,0x00000010 |
| Profile Abnormality | Circumscribed | 1,0x00000020 |
| Profile Abnormality | Microlobulated | 1,0x00000040 |
| Profile Abnormality | Obscured | 1,0x00000080 |
| Profile Abnormality | Indistinct | 1,0x00000100 |
| Profile Abnormality | Spiculated | 1,0x00000200 |
| Profile Abnormality | Intraductal | 1,0x00000400 |
| Profile Abnormality | Irregular | 1,0x00000800 |
| Profile Abnormality | Smooth | 1,0x00001000 |
| Profile Abnormality | High density | 1,0x00002000 |
| Profile Abnormality | Equal density | 1,0x00004000 |
| Size and Distance | Parallel/skin | 1,0x00800000 |
| Size and Distance | Perpendic/skin | 1,0x01000000 |
| Assoc Calcs | Generic calcs | 2,0x00000001 |
| Assoc Calcs | Amorphous | 2,0x00000002 |
| Assoc Calcs | Branching | 2,0x00000004 |
| Assoc Calcs | Coarse | 2,0x00000008 |
| Assoc Calcs | Dystrophic | 2,0x00000010 |
| Assoc Calcs | Eggshell | 2,0x00000020 |
| Assoc Calcs | Lucent-centered | 2,0x00002000 |
| Assoc Calcs | Milk of calcium | 2,0x00004000 |
| Assoc Calcs | Pleomorphic | 2,0x00008000 |
| Assoc Calcs | Punctate | 2,0x00010000 |
| Assoc Calcs | Rim | 2,0x00020000 |
| Assoc Calcs | Round | 2,0x00040000 |
| Assoc Calcs | Skin | 2,0x00080000 |
| Assoc Calcs | Spherical | 2,0x00100000 |
| Assoc Calcs | Suture | 2,0x00200000 |
| Assoc Calcs | Vascular | 2,0x00400000 |
| Assoc Calcs | Clustered | 2,0x00800000 |
| Assoc Calcs | Diffuse | 2,0x01000000 |
| Assoc Calcs | Grouped | 2,0x02000000 |
| Assoc Calcs | Linear | 2,0x04000000 |
| Assoc Calcs | Regional | 2,0x08000000 |
| Assoc Calcs | Scattered | 2,0x10000000 |
| Assoc Calcs | Segmental | 2,0x20000000 |
| Associated findings | Hematoma | 3,0x00000001 |
| Associated findings | Nipple retract | 3,0x00000002 |
| Associated findings | Seroma | 3,0x00000008 |
| Associated findings | Skin involvement | 3,0x00000010 |
| Associated findings | Skin lesion | 3,0x00000020 |
| Associated findings | Skin retraction | 3,0x00000040 |
| Associated findings | Skin thicken | 3,0x00000080 |
| Associated findings | Trab thicken | 3,0x00000100 |
| Change From Prior | Incr in size | 3,0x00000200 |
| Change From Prior | Decr in size | 3,0x00000400 |
| Change From Prior | Incr in calcs | 3,0x00002000 |
| Change From Prior | Decr in calcs | 3,0x00004000 |
| Change From Prior | Incr in number | 3,0x00008000 |
| Change From Prior | Decr in number | 3,0x00010000 |
| Change From Prior | Less prom. | 3,0x00020000 |
| Change From Prior | More prom. | 3,0x00040000 |
| Associated findings | Archit distortion | 3,0x00080000 |
| Associated findings | Axillary adenop | 3,0x00100000 |
| Associated findings | Chest wall invas | 3,0x00200000 |

The database of ROIs created from all examinations, detailed abnormalities, and pathology is generated and electronically stored at one or more sites. The information is then concatenated. As each exam and abnormality's result is created using the bitwise technique mentioned above, a search is made for an identical pathology finding with the identical set of bitset integer values (lexicon items) describing the abnormalities. If not found, a single record is created for each final abnormality pathology finding for each unique set of integer "lexicon" values. When duplicates are found, abnormality, benign, and malignant, the appropriate counters are incremented and the data displayed in profiler button 410 is updated.

In querying the database, the user selects lexicon items and/or pathology findings and the statistical system will instantly show "quick" statistics (total #'s only) in profiler button 410 for other exam abnormalities that "include" the profile of selected items. When the radiologist selects "round shape" he will instantly see statistics for all other abnormalities with a "round shape," noting how many were ultimately benign, how many were malignant, and how many were never biopsied. The radiologist can also view a statistical list of findings for all abnormalities with "round shape," perhaps helping determine probabilities for malignancy. If the radiologist subsequently also selects "spiculated margin," the same process will occur for all abnormalities with a "round shape" AND a "speculated margin."

An example embodiment can use a bit-setting method to produce a typical database that is small enough such that it can be loaded into the main memory of the MIS to enable rapid retrieval and updates. In an embodiment, the loading process is performed by a background thread during system startup allowing the user to continue working during loading. In querying the database, all the system needs to do is convert the currently selected lexicon items into their corresponding bitmap values, and then search the database using an "exclusive OR" (xor) comparison on the database records. A record matches when all the "set" bit values from the selected items are "set" in the database record being compared. Abnormality, Benign, and Malignant counts on each matching record are tabulated and ultimately presented to the radiologist.

The combination of the high-speed statistical comparison database and the ROI image database allows an embodiment of the system to provide a radiologist with images stored at a local facility for comparative diagnostic purposes. The system also allows a radiologist to select images based on the BI-RADS or other lexicon abnormality descriptors, allowing a comparison of additional images from a larger database or final pathology results if the abnormality was biopsied. Table 2 provides on exemplary mapping of BI-RADS values to the more efficiently stored and searched bit-field values.

TABLE 2

Mammogram Lexicon to BIRADS Conversion and Detailing

| ABNORMALITY | CLASSIFICATION | DESCRIPTOR ID NUMBER | DATABASE BIT-FIELD VALUE |
|---|---|---|---|
| Mass | | | |
| Shape | Irregular | 16 | 0x00000001 |
|  | Lobulated | 190 | 0x00000002 |
|  | Oval | 15 | 0x00000004 |
|  | Reniform | 27 | 0x00000008 |
|  | Round | 14 | 0x00000010 |
| Margin | Circumscribed | 109 | 0x00000020 |
|  | Microlobulated | 111 | 0x00000040 |
|  | Obscured | 28 | 0x00000080 |
|  | Indistinct | 21 | 0x00000100 |
|  | Spiculated | 29 | 0x00000200 |
|  | Intraductal | 201 | 0x00000400 |
|  | Irregular | 20 | 0x00000800 |
|  | Smooth | 18 | 0x00001000 |
| Density | High density | 211 | 0x00002000 |
|  | Equal density | 213 | 0x00004000 |
|  | Low density | 212 | 0x00008000 |
|  | Fat containing | 214 | 0x00010000 |
|  | Cent lucent | 215 | 0x00020000 |
| Wall | Septated internal wall | 25 | 0x00080000 |
|  | Irregular internal wall | 24 | 0x00100000 |
|  | Smooth internal wall | 23 | 0x00200000 |
|  | Thickened wall | 199 | 0x00400000 |
| Calcification Type | (generic calcs) | 701 | 0x00000001 |
|  | Amorphous | 702 | 0x00000002 |
|  | Branching | 703 | 0x00000004 |
|  | Coarse | 704 | 0x00000008 |
|  | Dystrophic | 705 | 0x00000010 |
|  | Eggshell | 706 | 0x00000020 |
|  | Fine | 707 | 0x00000040 |
|  | Heterogeneous | 708 | 0x00000100 |
|  | Indistinct | 709 | 0x00000200 |
|  | Large rodlike | 710 | 0x00000400 |
|  | Layering | 711 | 0x00000800 |
|  | Linear | 712 | 0x00001000 |
|  | Lucent-centered | 713 | 0x00002000 |
|  | Milk of calcium | 714 | 0x00004000 |
|  | Pleomorphic | 715 | 0x00008000 |
|  | Punctate | 716 | 0x00010000 |
|  | Rim | 717 | 0x00020000 |
|  | Round | 718 | 0x00040000 |
|  | Skin | 719 | 0x00080000 |
|  | Spherical | 720 | 0x00100000 |
|  | Suture | 721 | 0x00200000 |
|  | Vascular | 722 | 0x00400000 |
| Calcification Distribution | Clustered | 751 | 0x00800000 |
|  | Diffuse | 752 | 0x01000000 |
|  | Grouped | 753 | 0x02000000 |
|  | Linear | 754 | 0x04000000 |
|  | Regional | 755 | 0x08000000 |
|  | Scattered | 756 | 0x10000000 |
|  | Segmental | 757 | 0x20000000 |
| Foreign body, scar, or other (typically ignore) | Hematoma | 478 | 0x00000001 |
|  | Nipple retract | 477 | 0x00000002 |
|  | Post surgical scar | 479 | 0x00000004 |
|  | Seroma | 469 | 0x00000008 |
|  | Skin involvement | 252 | 0x00000010 |
|  | Skin lesion | 473 | 0x00000020 |
|  | Skin retraction | 251 | 0x00000040 |
|  | Skin thicken | 250 | 0x00000080 |
|  | Trab thicken | 470 | 0x00000100 |
| Changes from prior exam | Incr in size | 77 | 0x00000200 |
|  | Decr in size | 78 | 0x00000400 |
|  | Incr in calcs | 483 | 0x00002000 |
|  | Decr in calcs | 484 | 0x00004000 |
|  | Incr in number (mass) | 481 | 0x00008000 |
|  | Decr in number (mass) | 482 | 0x00010000 |
|  | Less prom. | 293 | 0x00020000 |
|  | More prom. | 294 | 0x00040000 |

The features provided by the system can also be combined with any one of several available computer aided diagnostic (CAD) products to validate, improve, and allow simplified testing of future CAD algorithms. A CAD product can be evaluated by using the electronically compiled descriptions of any abnormalities shown in a collection of ROI images to compare the CAD software algorithms against the real world pathology or biopsy results that were actually performed on the ROIs depicted in the image database.

Once the reliable performance of a CAD algorithm is established it may be used to further assist or confirm radiologist assessments of mammography images from new patients, or to alert the medical staff or radiologists when new or previously unclassified abnormalities are detected. Additionally, the integration of a CAD algorithm and the lexicon abnormality descriptors to generate ROI entries, such as those depicted in FIG. 6b, can pre-select the ROI classifications for each abnormality detected by a CAD product. This combination is especially advantageous as it reduces the number of radiologist provided entries to only corrections to the CAD interpretation of an ROI or any ROI that were not categorized initially by the CAD product. While a handful of mouse clicks or keyboard entries, or similar gestures, may seem trivial, the combined timesavings over the high volume of patient images that must be reviewed can yield a substantial savings in time, cost and comfort.

In the example embodiment discussed above, the display of the statistical results in profiler button 410 is automatically updated every time the radiologist enters or changes a data point. In an alternative embodiment, display window 410 is hidden, or the update suppressed, until the entry of all of the patient's data is complete. This alternative embodiment may be useful as a training tool for educating new radiologists by preventing them from being influenced by the statistical updates as they perform their entry of the data points for a patient.

Figure 7:
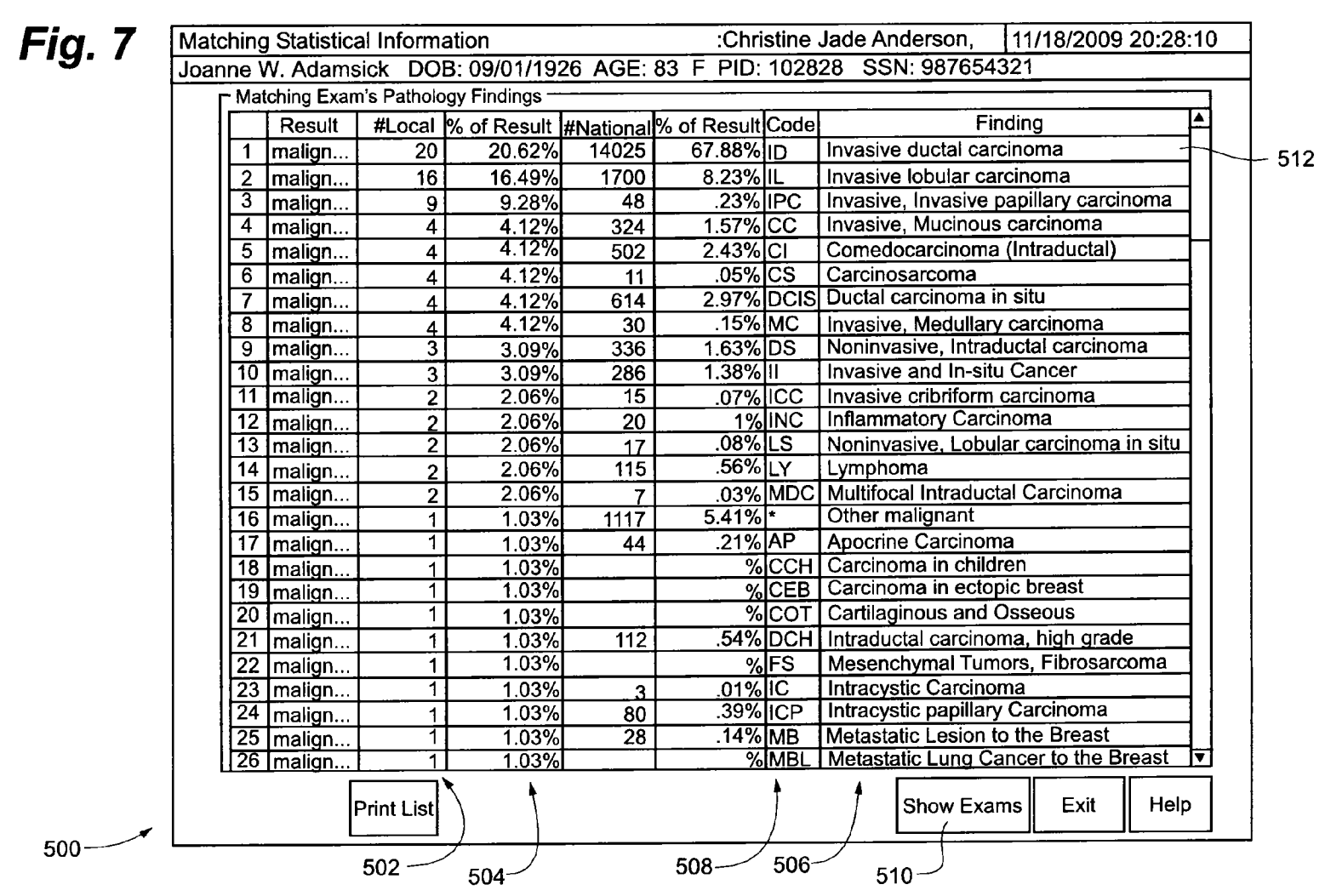

As shown in FIG. 7, when the user activates, or clicks on, the profiler button 410 of FIG. 6b, a window of matching statistical information 500 is displayed. This window of matching statistical information 500 includes the individual quantity 502 and the percentages 504 for malignant and benign outcomes in a sorted itemized list with both local and national data. Additionally, window 500 also includes the various pathology findings 506, as well as the code for that finding 508, contained in the database.

The example embodiment provides a "show exams" button 510 that allows a radiologist to retrieve the examinations for an individually selected pathology type 512. FIG. 8 depicts an examination list window 550 for the selected pathological type 512. The matching exams displayed in FIG. 8 are only those database records from the local facility database. Any records retrieved from a non-local database would not contain any patient identifying information. The embodiment of the MIS depicted here further provides the radiologist with the opportunity to select a record 560 of individual patient with the same diagnosis 512 for further review. The selection of the "View patient priors" button 570 directs the system to open a window containing the selected patient's examination record.

FIG. 9 depicts an exemplary prior exam window 600 displaying the images for an individual patient's exam. Prior exam window 600 includes historical exam images for the selected patient for referencing process of care. In another embodiment, a filter can be applied yielding all historical patient images. By selecting an individual exam report 602 and then one of the "View Full" 604, "Preview" 606, "Print" 608, or "Send to Viewstation" 610, the radiologist can examine the selected exam report 602 and optionally compare the images contained in that record to the current patient's images.

FIG. 10 depicts a patient report 700 summarizing the details of the CAD or radiologist findings from the examination and analysis of the patient's images. The report 700 can contain a clipped portion of the medical image or a thumbnail picture summarizing the ROI, as well as a multi-perspective wireframe guide that maps the location of the ROI onto the outline of the patient's anatomy.

FIG. 11 through FIG. 14 depict an exemplary embodiment of a standalone or web-based interface 800 to an embodiment of the profiler system. The web-based interface 800 can be accessed with any of the commonly available web browsers such as Microsoft Internet Explorer or Mozilla Firefox. As appreciated by those skilled in the art, a web-based interface may be hosted on a server connected to the Internet for use by a variety of geographically separated individuals or locally where access is limited to a particular facility's local network.

Figure 11:
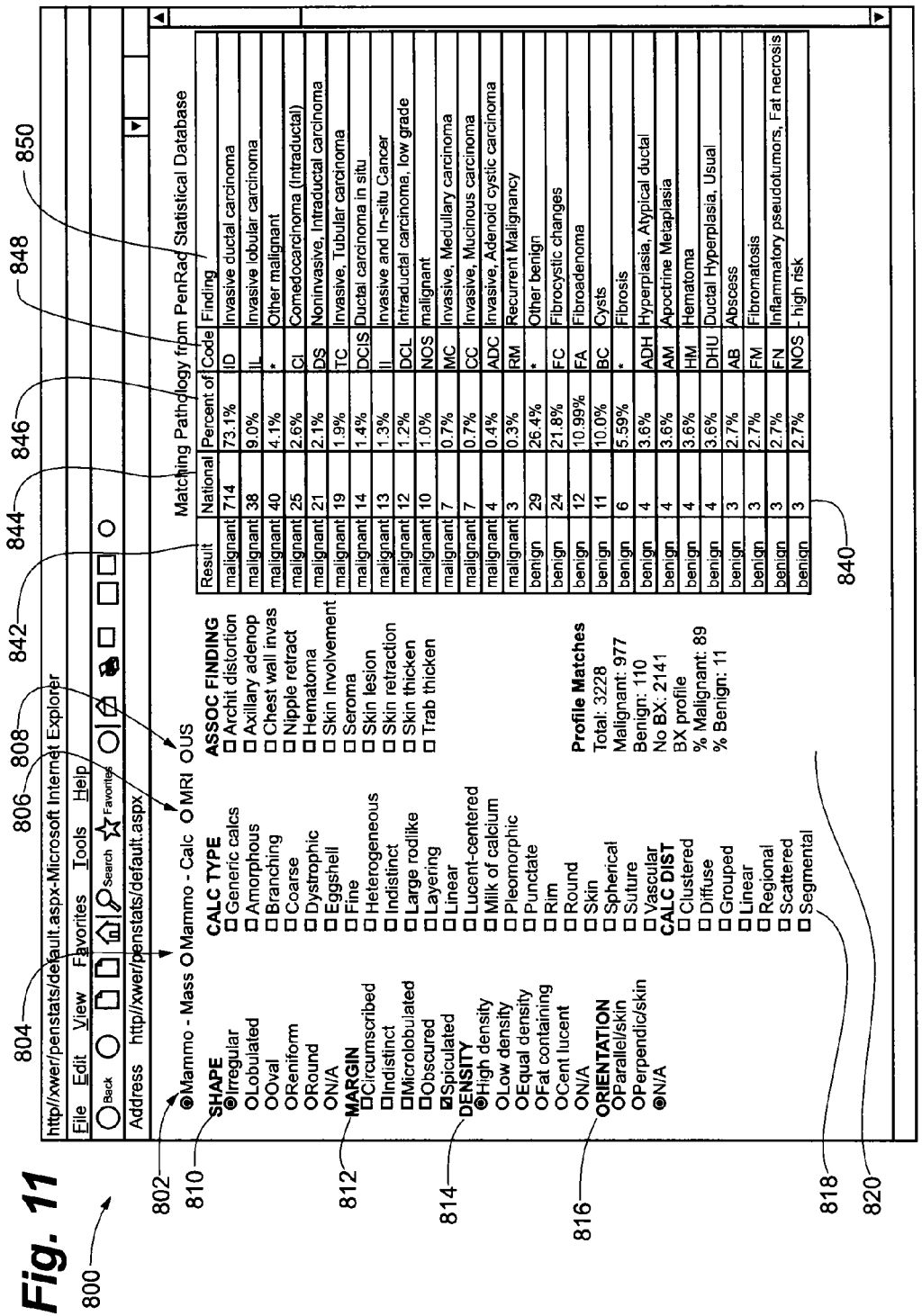
FIG. 11 is an example embodiment of a web-based form for use with an embodiment of the invention.

FIG. 11 depicts a web-based interface 800 providing a mechanism to select various characteristics regarding abnormality information contained in a database. Four modalities are presented, Mammogram-Mass 802, Mammogram-Calcification 804, MRI 806 and Ultrasound (US) 808. Depending on the modality selected, additional characteristics related to the selected modality are displayed to provide further details of the abnormality information request. The example depicted in FIG. 11 indicates a request for abnormality information contained in the database where the abnormality is categorized as a Mammogram-Mass 802, has an irregular shape 810, a speculated margin 812, and a high density 814. Mammogram-Mass 802 can also have associated calcification types 818.

As depicted in FIG. 12, the Mammogram-Calcification 804 modality is selected as the primary abnormality, and the "Mass" column containing the Shape 810, Margin 812, Density 814, and Orientation 816 categories, shown in FIG. 11, are removed from the interface 800. Interface 800 can include a results summary display area 820 and a matching pathology display area 840. The results summary display area 820, in a manner similar to the profiler button 410 of FIG. 6a, displays a count of matching abnormalities and their pathological outcome that were found in the database, as well as the percentages of the biopsied abnormalities that we either malignant or benign.

The matching pathology display area 840 can include a list of findings that can detail the percentages of a pathology diagnosis for abnormalities that were malignant or benign. The display area 840 example includes the result 842 as either malignant or benign, the number of entries 844 in the national database, the percentage 846 that each pathology represents of either the malignant or benign diagnosis, a pathology code 848 and a summary of the finding 850. Both the results summary display area 820 and the matching pathology display area 840 are updated whenever a new abnormality categorization is selected.

Figure 13:
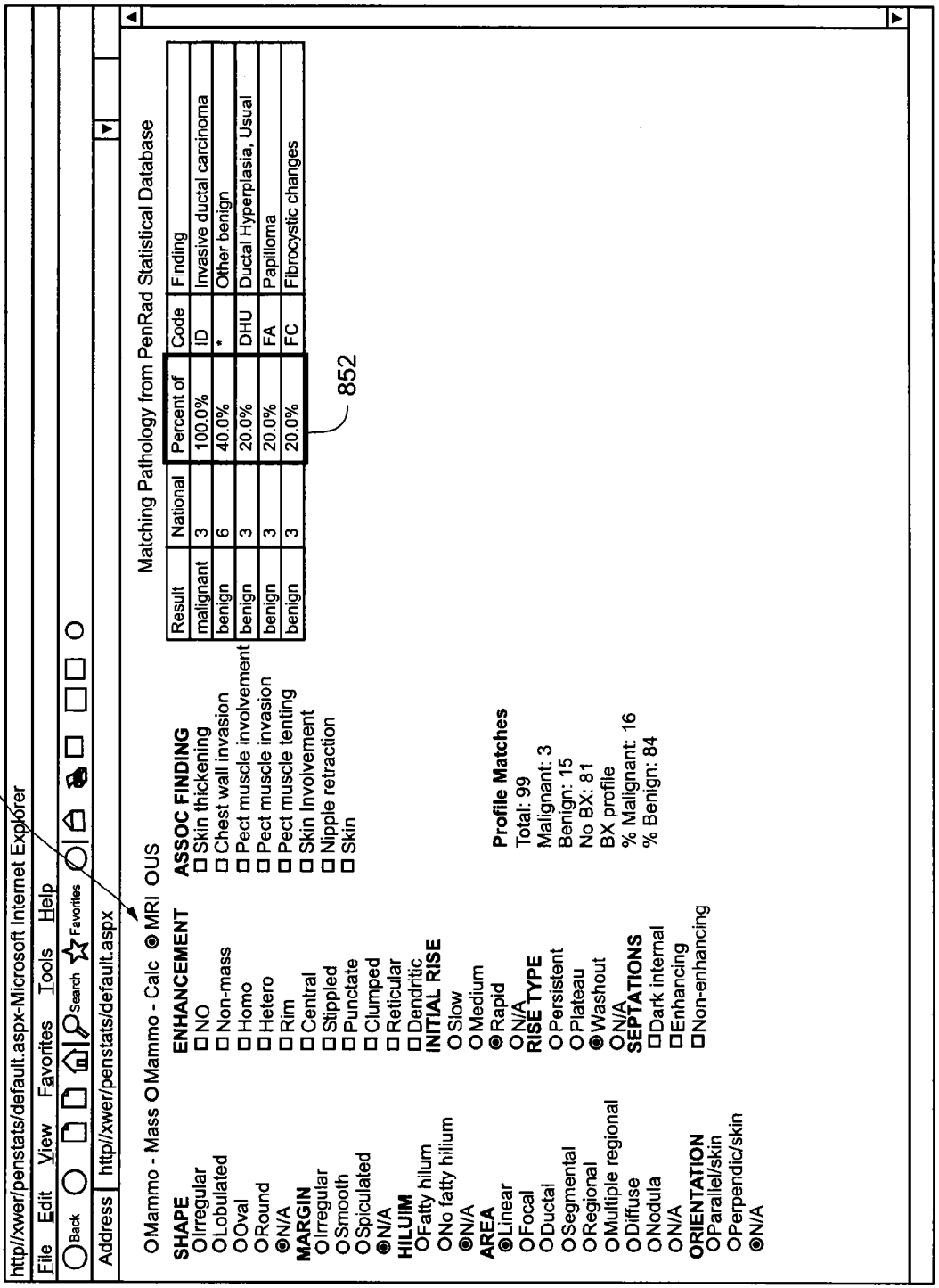
FIG. 13 is an example embodiment of a web-based form for use with an embodiment of the invention.

FIG. 13 depicts an example embodiment of interface 800 displaying categories that are related to the MRI 806 modality. As shown in the "Percent of" column 852 of the matching pathology display area 840, the percentages of the abnormality diagnosis are calculated as the number of relevant diagnosis from the total number of just the malignant or just the benign results. As shown, the percentages of malignant diagnosis equal 100% and the benign diagnosis equal 100%.

Figure 14:
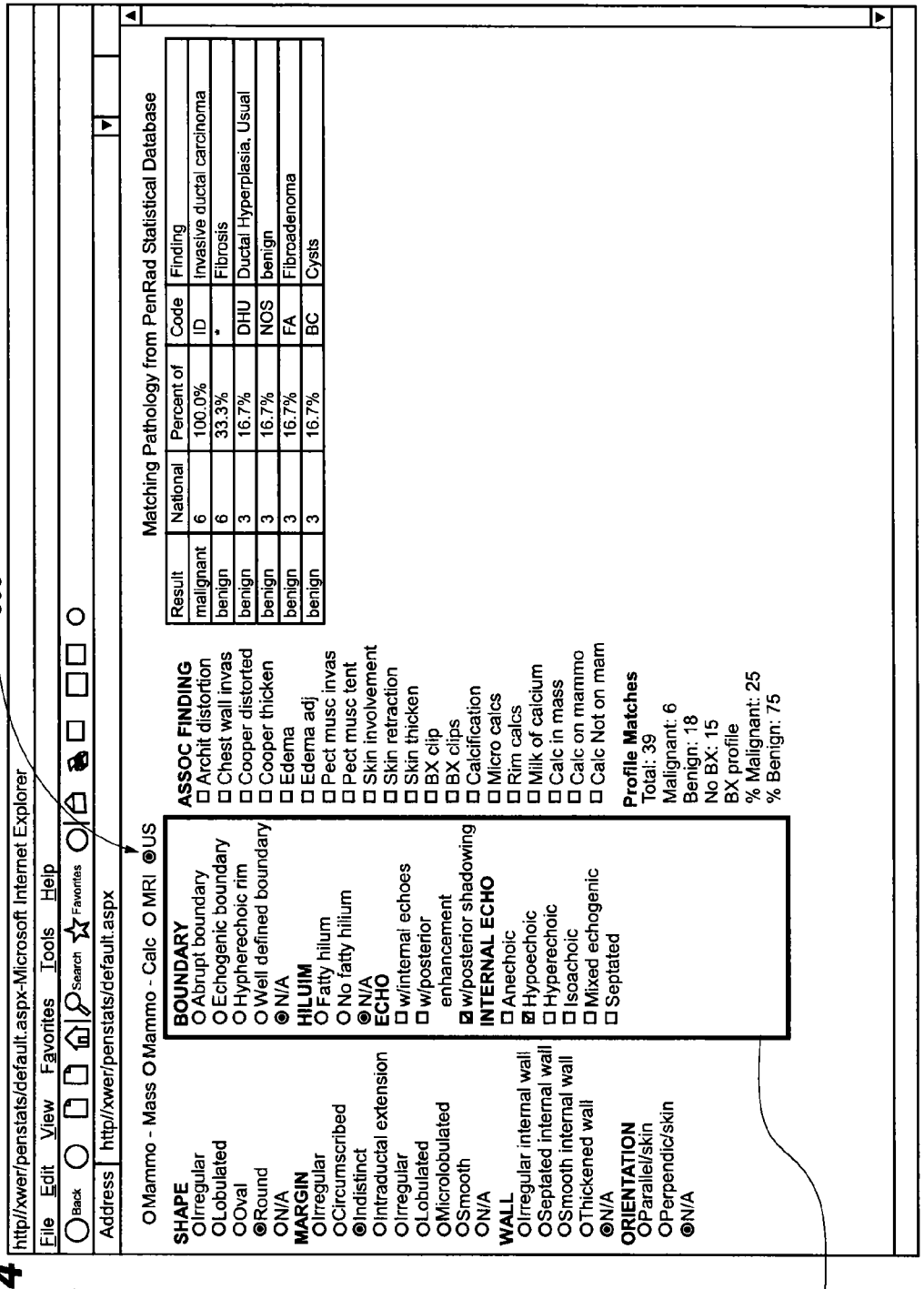
FIG. 14 is an example embodiment of a web-based form for use with an embodiment of the invention.

FIG. 14 depicts an example embodiment of interface 800 displaying categories that are related to the ultrasound 808 modality. The ultrasound 808 modality includes fields for "Boundary," "Hilum," "Echo," and "Internal Echo" in column 860 that are specific to ultrasound imaging techniques. It is contemplated that other fields, columns, or modalities can be added or presented as needed to accommodate the preferences of the user or to incorporate other new or existing diagnostic technologies.

The foregoing descriptions present numerous specific details that provide a thorough understanding of various embodiments of the invention. It will be apparent to one skilled in the art that various embodiments, having been disclosed herein, may be practiced without some or all of these specific details. In other instances, known components have not been described in detail in order to avoid unnecessarily obscuring the present invention. It is to be understood that even though numerous characteristics and advantages of various embodiments are set forth in the foregoing description, together with details of the structure and function of various embodiments, this disclosure is illustrative only. Other embodiments may be constructed that nevertheless employ the principles and spirit of the present invention. Accordingly, this application is intended to cover any adaptations or variations of the invention. It is manifestly intended that this invention be limited only by the following claims and equivalents thereof.

For purposes of interpreting the claims for the present invention, it is expressly intended that the provisions of Section 112, sixth paragraph of 35 U.S.C. are not to be invoked with respect to a given claim unless the specific terms "means for" or "step for" are recited in that claim.

Any incorporation by reference of documents above is limited such that no subject matter is incorporated that is contrary to the explicit disclosure herein. Any incorporation by reference of non-priority documents above is further limited such that no claims included in the documents are incorporated by reference herein and any definitions provided in the documents are not incorporated by reference herein unless expressly included herein.

The invention claimed is:

1. A method comprising:
providing a first database of existing categorizations of existing abnormalities within a first medical facility, each existing categorization comprising at least one characteristic identified for each existing abnormality;
providing a second database of existing categorizations of existing abnormalities within a plurality of medical facilities, each existing categorization comprising at least one characteristic identified for each existing abnormality;
defining a region of interest in a breast-tissue image, wherein the region of interest contains a breast-tissue abnormality;
obtaining a categorization of the abnormality by identifying at least one characteristic of the abnormality contained in the region of interest;
identifying, by a computer system, all existing categorizations in the first database matching the categorization of the abnormality;
identifying, by the computer system, all existing categorizations in the second database matching the categorization of the abnormality;
presenting, by the computer system, an adjacent display of:
a total quantity of the indentified existing categorizations in the first database matching the categorization of the abnormality,
a quantity of the identified existing categorizations in the first database matching the categorization of the abnormality that are benign,
a quantity of the identified existing categorizations in the first database matching the categorization of the abnormality that are malignant,
a total quantity of the indentified existing categorizations in the second database matching the categorization of the abnormality,
a quantity of the identified existing categorizations in the first second database matching the categorization of the abnormality that are benign, and
a quantity of the indentified existing categorizations in the second database matching the categorization of the abnormality that are malignant.

2. The method of claim 1, wherein identifying at least one characteristic comprises manually identifying at least one characteristic of the abnormality.

3. The method of claim 1, wherein identifying at least one characteristic comprises utilizing a computer assisted diagnostic tool to identify at least one characteristic of an abnormality contained in the region of interest.

4. The method of claim 1, wherein identifying at least one characteristic comprises selecting the at least one characteristic from a lexicon of abnormality characteristics.

5. The method of claim 4, further comprising synthesizing, by the computer system, the lexicon of abnormality characteristics with a lexicon of the existing categorizations.

6. The method of claim 1, wherein obtaining a categorization comprises:
obtaining a manual categorization of a region of interest;
obtaining a computer assisted diagnostic system categorization of the region of interest; and
comparing the manual categorization and the computer assisted diagnostic system categorization.

7. The method of claim 1, further comprising providing, by the computer system, an image of a breast tissue abnormality having an existing categorization that matches the categorization of the region of interest.

8. The method of claim 1, wherein the first and second databases of existing categorizations of regions of interest each includes a first sub-set of the regions of interest that are known to be malignant and a second sub-set of the regions of interest that are known to be benign.

9. The method of claim 1, further comprising:
presenting, by the computer system, one or more exam pathology findings for the current categorization, each of the one or more exam pathology findings including:
a benign or malignant outcome,
a quantity corresponding to the individual pathology finding, and
a description of the finding.

10. The method of claim 9, further comprising:
receiving a selected pathology finding from the one or more exam pathology findings;
presenting, by the computer system, one or more examinations for the selected pathology finding corresponding to at least one historical patient having the same selected pathology finding, the one or more examinations each including a patient identifier;
receiving a selected patient identifier corresponding to a selected historical patient having the same selected pathology finding; and
presenting, by the computer system, an historical examination report for the selected historical patient.

11. A medical breast image profiler comprising:
a first database of existing categorizations of existing abnormalities in regions of interest in breast images within a first medical facility, each existing categorization comprising at least one characteristic identified for each existing abnormality;
a second database of existing categorizations of existing abnormalities in regions of interest in breast images within a plurality of medical facilities, each existing categorization comprising at least one characteristic identified for each existing abnormality;
a graphical user interface configured to present a plurality of possible characteristics according to which a current categorization of a region of interest in a breast image can be defined; and
a processor configured to identify all existing categorizations in the first database that match the current categorization, identify all existing categorization in the second database that match the current categorization, and to present information related to the identification in the graphical user interface,
wherein the graphical user interface comprises a profiler display portion, and wherein the information related to the identification is presented in the profiler display portion by an adjacent display of:
a total quantity of the identified existing categorizations in the first database matching the current categorization,
a quantity of the identified existing categorizations in the first database matching the current categorization that are benign, a quantity of the identified existing categorizations in the first database matching the current categorization that are malignant, a total quantity of the identified existing categorizations in the second database matching the current categorization, a quantity of the identified existing categorizations in the second database matching the current categorization that are benign, and a quantity of the identified existing categorizations in the second database matching the current categorization that are malignant.

12. The profiler of claim 11, wherein the graphical user interface is presented in a web browser.

13. The profiler of claim 11, wherein the processor is configured to dynamically update the information related to the identification presented in the graphical user interface if selected ones of the plurality of possible characteristics are changed.

14. The profiler of claim 11, wherein the graphical user interface is further configured to present one or more exam pathology findings for the current categorization, each of the one or more exam pathology findings including;
   a benign or malignant outcome,
   a quantity corresponding to the individual pathology finding, and
   a description of the finding.

15. The profiler of claim 14, wherein the processor is further configured to receive a selected pathology finding from the one or more exam pathology findings, and the graphical user interface is further configured to present one or more examinations for the selected pathology finding corresponding to at least one historical patient having the same selected pathology finding, the one or more examinations each including a patient identifier.

16. The profiler of claim 15, wherein the processor is further configured to receive a selected patient identifier corresponding to a selected historical patient having the same selected pathology finding, and the graphical user interface is further configured to present an historical examination report for the selected historical patient.

17. A breast image profiler comprising:
   a first database of existing categorizations of existing abnormalities in regions of interest in breast tissue images within a first medical facility, each existing categorization comprising at least one characteristic identified for each existing abnormality;
   a second database of existing categorizations of existing abnormalities in regions of interest in the breast images within a plurality of medical facilities, each existing categorization comprising at least one characteristic identified for each existing abnormality;
   a graphical user interface presented in a web browser and configured to present a plurality of possible characteristics according to which a region of interest in a breast tissue image can be characterized; and
   a processor configured
      to identify all existing categorizations in the first database that match selected ones of the plurality of possible characteristics,
      to identify all existing categorizations in the second database that match selected ones of the plurality of possible characteristics, and
      to calculate a rate of at least one of malignancy or benignity for the selected ones of the plurality of possible characteristics based on a comparison with the existing categorizations for each of the first and second databases, and
      to present information related to the identification in the graphical user interface by an adjacent display of;
         a total quantity of the identified existing categorizations in the first database matching the selected ones of the plurality of possible characteristics,
         a quantity of the identified existing categorizations in the first database matching the selected ones of the plurality of possible characteristics that are benign,
         a quantity of the identified existing categorizations in the first database matching the selected ones of the plurality of possible characteristics that are malignant,
         a total quantity of the identified existing categorizations in the second database matching the selected ones of the plurality of possible characteristics,
         a quantity of the identified existing categorizations in the second database matching the selected ones of the plurality of possible characteristics that are benign, and
         a quantity of the identified existing categorizations in the second database matching the selected ones of the plurality of possible characteristics that are malignant.

18. The breast image profiler of claim 17, wherein the graphical user interface is configured to update a display of statistical report rate of at least one of malignancy or benignity based on the selection of one of the plurality of possible characteristics.

19. A multiple modality tissue image profiler comprising:
   a first database of existing pathological findings for a plurality of tissue abnormalities within a first medical facility, each tissue abnormality located in a region of interest of one of a plurality of tissue images, each existing pathological finding comprising at least one characteristic identified for each tissue abnormality;
   a second database of existing pathological findings for a plurality of tissue abnormalities within a plurality of medical facilities, each tissue abnormality located in a region of interest of one of a plurality of tissue images, each existing pathological finding comprising at least one characteristic identified for each tissue abnormality;
   a graphical user interface configured to present a plurality of possible characteristics according to which a tissue abnormality can be characterized; and
   a processor configured
      to identify all existing categorizations in the first database that match selected ones of the plurality of possible characteristics,
      to identify all existing categorizations in the second database that match selected ones of the plurality of possible characteristics,
      to present information related to the matching selected ones of the plurality of possible characteristics by an adjacent display of;
         a total quantity of the identified existing categorizations in the first database matching the selected ones of the plurality of possible characteristics,
         a quantity of the identified existing categorization in the first database matching the selected ones of the plurality of possible characteristics that are benign,
         a quantity of the identified existing categorizations in the first database matching the selected ones of the plurality of possible characteristics that are malignant, a total quantity of the identified existing categorizations in the second database matching the selected ones of the plurality of possible characteristics, a quantity of the identified existing categorizations in the second database matching the selected ones of the plurality of possible characteristics that are benign, and a quantity of the identified existing categorizations in the second database matching the selected ones of the plurality of the possible characteristics that are malignant, to retrieve at least one image having at least one of the selected ones of the plurality of possible characteristics based on a comparison with the existing categorizations, and to present the at least one image depicting the characterized tissue abnormality in the graphical user interface:

wherein the plurality of images depicting the characterized tissue abnormality include a plurality of different imaging modalities.

20. The profiler of claim 19, wherein the plurality of different imaging modalities are selected from the group consisting of an X-ray, MRI image, an ultrasound image, a CT image and a pathologic image.

* * * * *